US012746241B2

(12) United States Patent
Jiang et al.

(10) Patent No.: US 12,746,241 B2
(45) Date of Patent: Sep. 29, 2026

(54) SOLID PHARMACEUTICAL PREPARATION, PREPARATION METHOD THEREFOR AND USE THEREOF

(71) Applicants: SHANGHAI HAIYAN PHARMACEUTICAL TECHNOLOGY CO., LTD., Shanghai (CN); YANGTZE RIVER PHARMACEUTICAL GROUP CO., LTD., Taizhou (CN)

(72) Inventors: Taotao Jiang, Shanghai (CN); Jibiao Wang, Shanghai (CN); Han Yang, Shanghai (CN); Li Li, Shanghai (CN); Zhaoling Dan, Shanghai (CN); Keyi Zhu, Shanghai (CN); Zhenya Zeng, Shanghai (CN); Bo Su, Shanghai (CN); Xi Chen, Shanghai (CN)

(73) Assignees: SHANGHAI HAIYAN PHARMACEUTICAL TECHNOLOGY CO., LTD., Shanghai (CN); YANGTZE RIVER PHARMACEUTICAL GROUP CO., LTD., Taizhou (CN)

( * ) Notice: Subject to any disclaimer, the term of this patent is extended or adjusted under 35 U.S.C. 154(b) by 851 days.

(21) Appl. No.: 17/919,402

(22) PCT Filed: Apr. 14, 2021

(86) PCT No.: PCT/CN2021/087262

§ 371 (c)(1),
(2) Date: Oct. 17, 2022

(87) PCT Pub. No.: WO2021/208976

PCT Pub. Date: Oct. 21, 2021

(65) Prior Publication Data

US 2023/0149402 A1 May 18, 2023

(30) Foreign Application Priority Data

Apr. 17, 2020 (CN) ......................... 202010304917.6
Dec. 29, 2020 (CN) ......................... 202011594757.X

(51) Int. Cl.

| | |
|---|---|
| ***A61K 31/506*** | (2006.01) |
| ***A61K 9/00*** | (2006.01) |
| ***A61K 9/14*** | (2006.01) |
| ***A61K 9/20*** | (2006.01) |
| ***A61K 31/46*** | (2006.01) |

(Continued)

(52) U.S. Cl.

CPC .......... *A61K 31/506* (2013.01); *A61K 9/0053* (2013.01); *A61K 9/2009* (2013.01); *A61K 9/2027* (2013.01); *A61K 9/205* (2013.01); *A61K 9/2054* (2013.01)

(58) Field of Classification Search

CPC .. A61K 31/506; A61K 9/0053; A61K 9/2009; A61K 9/2027; A61K 9/205; A61K 9/2054; A61K 9/14; A61K 9/2013; A61K 9/2018; A61K 31/04; A61P 11/00; A61P 25/20; A61P 25/22; A61P 25/30

See application file for complete search history.

(56) References Cited

U.S. PATENT DOCUMENTS 10,100,047 B2 * 10/2018 He .......................... A61P 11/08
2018/0235965 A1 8/2018 Wu et al.

FOREIGN PATENT DOCUMENTS

CN 105209468 B 9/2017
EA 028386 B1 11/2017

(Continued)

OTHER PUBLICATIONS

Healthline, Tablet vs Capsules, https://www.healthline.com/health/capsule-vs-tablet, Feb. 2020 (Year: 2020).*

(Continued)

*Primary Examiner* — Bruck Kifle
*Assistant Examiner* — Kevin S Martin
(74) *Attorney, Agent, or Firm* — Umberg Zipser LLP; Priti Phukan

(57) ABSTRACT

The present invention relates to a solid pharmaceutical preparation and a preparation method therefor. Specifically, disclosed are a solid pharmaceutical preparation that comprises an orexin receptor antagonist compound and a preparation method therefor, the solid pharmaceutical preparation comprising an active ingredient of a compound represented by formula I, a filler, a binder, a disintegrant, and a lubricant. The solid pharmaceutical preparation has good dissolution, stability and in vivo bioavailability.

(I)

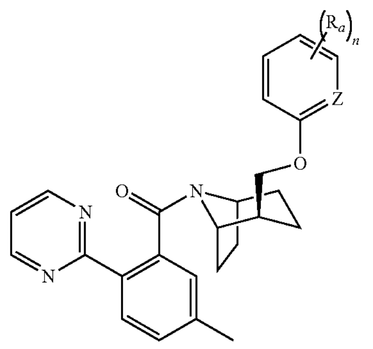

20 Claims, 5 Drawing Sheets

(51) Int. Cl.

| | |
|---|---|
| ***A61P 11/00*** | (2006.01) |
| ***A61P 25/20*** | (2006.01) |
| ***A61P 25/22*** | (2006.01) |
| ***A61P 25/30*** | (2006.01) |

(56) References Cited

FOREIGN PATENT DOCUMENTS

| | | | |
|---|---|---|---|
| EP | 1531805 | B1 | 4/2008 |
| EP | 3115362 | A1 | 1/2017 |
| EP | 3336088 | A1 | 6/2018 |
| JP | 2009543803 | A | 12/2009 |
| JP | 2017507185 | A | 3/2017 |
| JP | 2018525395 | A | 9/2018 |
| KR | 20090031618 | A | 3/2009 |
| KR | 20160143668 | A | 12/2016 |
| RU | 2669701 | C2 | 10/2018 |
| RU | 2703297 | C2 | 10/2019 |
| WO | 2007014124 | A2 | 2/2007 |
| WO | 2008008879 | A2 | 1/2008 |
| WO | 2014072961 | A2 | 5/2014 |
| WO | 2015131773 | A1 | 9/2015 |
| WO | 2017028732 | A1 | 2/2017 |
| WO | 2017072264 | A1 | 5/2017 |

OTHER PUBLICATIONS

Healthline, Tablets vs. Capsules, Feb. 2020 (Year: 2020).*

Tran, Size Does matter: The Importance of Micronized Drugs, Harbor Compounding Pharmacy, 2019 (Year: 2019).*

Abad VC, Guilleminault C. Insomnia in Elderly Patients: Recommendations for Pharmacological Management. Drugs Aging. Sep. 2018;35(9):791-817. doi: 10.1007/s40266-018-0569-8. PMID: 30058034. (Year: 2018).*

Chu et al., "Effect of Particle Size on the Dissolution Behaviors of Poorly Water-soluble Drugs," Arch Parm Res, 2012; 35(7):1187-1195.

Extended European Search Report for Application No. 21788226.5 dated Apr. 11, 2024; 10 pgs.

Chen et al., "Dissolution Rate," Pharmaceutics, Xi'An Jiaotong University Press, Jan. 31, 2014 1st edition, ISBN 978-7-5605-5501-0, p. 350, 22 pages.

PCT International Search Report and Written Opinion, International Application No. PCT/CN2021/087262, filing date Apr. 14, 2021, 9 pages.

First Office Action for Singapore Application No. 11202253983J dated Jul. 28, 2025; 11 pgs.

Notice of Allowance for Korean Patent Application No. 10-2022-7033065 issued Sep. 29, 2025; 3 pgs.

Office Action for Japanese Patent Application No. 2022-562168 dated Oct. 3, 2023, Machine Translation; 3 pgs.

Office Action for Russian Federation Application No. 2022129788 dated Jun. 19, 2023, Machine Translation; 29 pgs.

* cited by examiner

SOLID PHARMACEUTICAL PREPARATION, PREPARATION METHOD THEREFOR AND USE THEREOF

TECHNICAL FIELD

The invention belongs to the field of pharmaceutical formulation, and in particular relates to a solid pharmaceutical formulation comprising an orexin receptor antagonist compound, a preparation method thereof, and use in the manufacture of a medicament for treating an orexin-associated disease.

BACKGROUND OF THE INVENTION

Orexin (hypocretin) includes two neuropeptides produced in the hypothalamus: orexin A (OX-A) (a peptide containing 33 amino acids) and orexin B (OX-B) (a peptide containing 28 amino acids) (Sakurai T. et al, Cell, 1998, 92, 573-585). It is discovered that orexin stimulates food consumption in rats, which suggests that these peptides have a physiological role as mediators in central feedback mechanisms regulating feeding behavior (Sakurai T. et al., Cell, 1998, 92, 573-585). Orexin can regulate the state of sleep and insomnia, potentially proposing a new method for treating narcolepsy or insomniac in patients (Chemelli R. M. et al., Cell, 1999, 98, 437-451). Orexin also plays roles in arousal, motivation, learning and memory (Harris, et al, Trends Neurosci., 2006, 29(10), 571-577). In mammals, two orexin receptors have been cloned and characterized: the orexin-1 receptor and the orexin-2 receptor. They belong to the G protein-coupled receptor superfamily (Sakurai T. et al., Cell, 1998, 92, 573-585), in which the orexin-1 receptor (OX or OX1R) is selective for OX-A, and the orexin-2 receptor (OX2 or OX2R) is capable of binding to OX-A as well as OX-B. It is believed that the physiological roles of orexin are achieved through the expression of one or both of the OX1 receptor and OX2 (two subtypes of orexin receptors).

Orexin receptor can be found in the brain of warm-blooded animals and are associated with disorders such as: depression; anxiety; addiction; obsessive-compulsive disorder; affective neurosis; depressive neurosis; anxiety neurosis; psychotic depression disorder; behavior disorder; mood disorder; sexual dysfunction; psychosexual disorder; gender disorder; schizophrenia; manic depression; insanity; dementia; severe mental retardation and dyskinesia, such as Huntington's disease and Tourette syndrome; eating disorder such as anorexia, bulimia, cachexia, and obesity; addictive eating behavior; binge eating behavior; cardiovascular disease; diabetes; appetite/taste disorder; emesis, vomiting, nausea; asthma; cancer; Parkinson's disease; Cushing's syndrome/disease; basophilic adenomas; prolactinomas; hyperprolactinemia; pituitary gland tumor/adenomas; hypothalamic disorder; inflammatory bowel disease; stomach dysfunction; stomach ulcer; adiposogenital dystrophy; anterior pituitary disorder; pituitary disorder; anterior pituitary hypofunction; anterior pituitary hyperfunction; hypothalamic hypogonadism; Kallmann Syndrome (anosmia, hyposmia); functional or psychogenic amenorrhea; hypopituitarism; hypothalamic hypothyroidism; hypothalamus-adrenal dysfunction; sudden hyperprolactinemia; hypothalamic growth hormone deficiency; sudden growth deficiency; dwarfism; gigantism; acromegaly; disturbed biological and circadian rhythms; sleep disturbances associated with disorders such as insanity, neuropathic pain, and restless legs syndrome; heart and lung disease, acute and congestive heart failure; hypotension; hypertension; urine retention; osteoporosis; angina pectoris; acute myocardial infarction; ischemic or hemorrhagic stroke; arachnoid hemorrhage; ulcers; allergy; benign prostatic hypertrophy; chronic renal failure; kidney disease; impaired glucose tolerance; migraine; hyperalgesia; pain; increased or exaggerated sensitivity to pain, such as hyperalgesia, burning pain and allodynia; acute pain; burning pain; atypical facial pain; neuropathic pain; back pain; complex regional pain syndromes I and II; arthritis pain; sport trauma pain; pain associated with infections such as HIV, post-chemotherapy pain; post-stroke pain; postoperative pain; neuralgia; emesis, nausea, vomiting; conditions associated with visceral pain, such as irritable bowel syndrome and angina; migraine; bladder incontinence, such as urge incontinence; tolerance to narcotic or withdrawal from narcotic; sleep disorder; sleep apnea; narcolepsy; insomnia; parasomnia; jet lag syndrome; and neurodegenerative disorder, including disease classification entities such as disinhibition-dementia-Parkinson's disease-muscular dystrophy syndrome; epilepsy; seizure disorder and other diseases associated with common dysfunction of the orexin system.

CN106414439A discloses a class of piperidine derivatives as the orexin receptor antagonists, which have significant inhibitory effect on OX1 and OX2 GPCR receptor. It is found in the study that when they are prepared into solid pharmaceutical compositions, there are disadvantages of lower dissolution rate and dissolution level, as well as lower bioavailability and longer in vivo half-life, whereas long half-life of drugs for treating insomnia clearly has adverse effects, such as a residual effect on the second day, resulting in adverse consequences for the patients. Therefore, it is necessary to develop it into a solid pharmaceutical dosage form with higher dissolution rate and dissolution level, as well as higher bioavailability and lower half-life, in order to meet wider clinical administration requirements.

SUMMARY OF THE INVENTION

The object of the present invention is to provide a solid pharmaceutical formulation comprising the compound of formula I with a good stability, a good dissolution effect and a good bioavailability.

The first aspect of the present invention provides a solid pharmaceutical formulation, wherein the solid pharmaceutical formulation comprises an active ingredient, and the active ingredient is a compound represented by formula (I) or a pharmaceutically acceptable salt thereof, or a mixture of both;

(I)

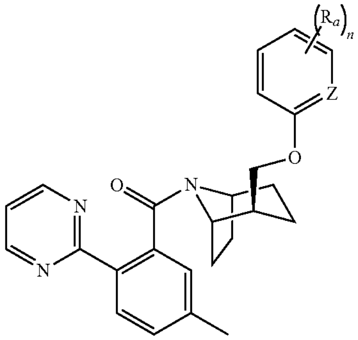

wherein $R^a$ is hydrogen, fluorine, chlorine, methyl, ethyl, propyl, isopropyl, methoxy, ethoxy, propoxy or isopropoxy;

Z is N or $CR_0$; $R_0$ is hydrogen, halogen or $C_{1-3}$ alkyl;

n is 0, 1 or 2;

and the particle size of the active ingredient is D90≤50 μm.

In another preferred example, the particle size of the active ingredient is D90≤35 μm. In another preferred example, the particle size of the active ingredient is D90≤30 μm. In another preferred example, the particle size of the active ingredient is D90≤20 μm. In another preferred example, the particle size of the active ingredient is D90≤10 μm. In another preferred example, the particle size of the active ingredient is D90=1 μm to 30 μm. In another preferred example, the particle size of the active ingredient is D90=1 μm to 20 μm. In another preferred example, the particle size of the active ingredient is D90=1 μm to 10 μm or D90=10 μm to 20 μm.

In another preferred example, the compound represented by formula (I) is a compound of formula (II):

(II)

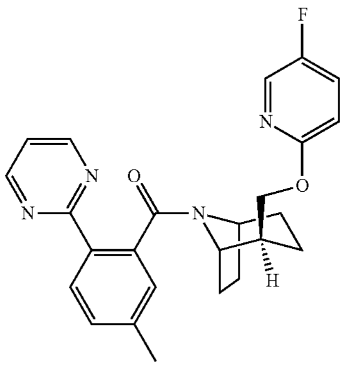

((1S,2R,5S)-2-(((5-fluoropyridin-2-yl)oxy)methyl)-8-azabicyclo[3.2.1]octan-8-yl)(5-methyl-2-(pyrimidin-2-yl)phenyl)methanone. As described in patent CN106414439A, the intracellular calcium signal change is detected by FLIPR and indicated by the $IC_{50}$ value of the compound to evaluate the inhibitory effect of the compound of formula (II) on OX1 and OX2 GPCR receptors, and the activities thereof are 20 nM (hOX1R) and 36 nM (hOX2R), respectively.

The pharmaceutically acceptable salt of the present invention includes pharmaceutically acceptable acid addition salt and pharmaceutically acceptable base addition salt. The pharmaceutically acceptable acid addition salt refers to a salt formed by an inorganic or organic acid which can retain the biological effectiveness of the free base without other side effects. The inorganic acid salt includes but is not limited to hydrochloride, hydrobromide, sulfate, phosphate and the like. The organic acid salt includes but is not limited to formate, acetate, propionate, glycolate, gluconate, lactate, oxalate, maleate, succinate, fumarate, tartrate, citrate, glutamate, aspartate, benzoate, mesylate, p-toluenesulfonate, salicylate and the like. These salts can be prepared by methods known in the art. The pharmaceutically acceptable base addition salt includes but is not limited to a salt of an inorganic base such as sodium salt, potassium salt, calcium salt, magnesium salt and the like, and includes but is not limited to a salt of an organic base such as ammonium salt, triethylamine salt, lysine salt, arginine salt and the like. These salts can be prepared by methods known in the art.

The compound represented by formula (I) and formula (II) of the present invention or the pharmaceutically acceptable salt thereof can be in any form, and the specific form includes but is not limited to amorphous, any crystalline form, hydrate, solvate and the like. In some embodiments, the compound represented by formula (II) exists in crystalline form A with Cu-Kα radiation XRPD spectrum thereof resolved as follows, and structure thereof shown in FIG. 6.

| Diffraction Angle 2θ | Relative Intensity (%) |
|---|---|
| 10.428 | 60.0 |
| 11.968 | 100.0 |
| 13.542 | 17.8 |
| 14.238 | 3.4 |
| 14.767 | 12.1 |
| 15.851 | 73.9 |
| 16.818 | 72.0 |
| 18.003 | 9.2 |
| 19.087 | 2.1 |
| 19.755 | 47.6 |
| 20.900 | 25.7 |
| 22.652 | 2.9 |
| 23.858 | 49.2 |
| 24.844 | 23.2 |
| 25.533 | 8.2 |
| 26.083 | 11.0 |
| 27.133 | 3.1 |
| 27.506 | 17.7 |
| 28.316 | 3.0 |
| 29.557 | 2.2 |
| 30.740 | 4.2 |
| 31.846 | 5.1 |
| 32.550 | 2.0 |
| 33.775 | 3.1 |
| 34.682 | 2.2 |
| 36.422 | 3.4 |
| 36.953 | 3.4 |
| 38.569 | 3.0 |

In some embodiments, the compound represented by formula (II) exists in crystalline form B with Cu-Kα radiation XRPD spectrum thereof resolved as follows, and structure thereof shown in FIG. 7.

| Diffraction Angle 2θ | Relative Intensity (%) |
|---|---|
| 8.611 | 100.0 |
| 10.330 | 70.6 |
| 12.284 | 13.4 |
| 13.703 | 23.9 |
| 14.057 | 5.6 |
| 14.351 | 4.8 |
| 14.848 | 9.2 |
| 15.576 | 7.5 |
| 16.602 | 31.6 |
| 17.250 | 71.3 |
| 17.902 | 90.7 |
| 18.277 | 42.4 |
| 19.149 | 6.5 |
| 20.625 | 21.7 |
| 21.550 | 42.7 |
| 22.124 | 2.3 |
| 23.307 | 33.4 |
| 23.953 | 2.6 |
| 24.370 | 32.3 |
| 26.501 | 29.4 |
| 26.915 | 8.7 |
| 27.663 | 11.0 |
| 27.939 | 15.5 |
| 29.499 | 2.6 |
| 30.604 | 3.2 |

-continued

| Diffraction Angle 2θ | Relative Intensity (%) |
|---|---|
| 31.727 | 13.3 |
| 32.969 | 2.6 |
| 33.378 | 2.8 |
| 33.777 | 3.0 |
| 34.825 | 1.6 |
| 36.399 | 5.3 |
| 37.366 | 4.3 |
| 39.357 | 3.3 |

The crystalline form A and the crystalline form B mentioned in the present invention can be prepared and characterized with reference to the method described in the patent CN107709318A. In some embodiments, the compound of formula (II) exists in a crystalline form with a single crystal X-ray diffraction spectrum thereof indicating that the compound of formula (II) has a three-dimensional ellipsoid structure as shown in FIG. 10.

In another preferred example, the content of the active ingredient is 1%-15%, more preferably 4%-10%, more preferably 9.5%-10% based on the total dry weight of the solid pharmaceutical formulation.

In another preferred example, the solid pharmaceutical formulation further comprises a binder selected from the group consisting of hypromellose, hydroxypropyl cellulose, povidone, sodium alginate, carbopol, polyvinyl alcohol and a combination thereof. The content of the binder is 0.5%-10%, more preferably 1.5%-3% based on the total dry weight of the solid pharmaceutical formulation.

In another preferred example, the binder is selected from the group consisting of hypromellose-E5, hypromellose-K4M, hypromellose-E50, carbopol, polyvinyl alcohol and a combination thereof.

In another preferred example, the binder is hypromellose-E5.

In another preferred example, the solid pharmaceutical formulation further comprises a filler selected from the group consisting of microcrystalline cellulose, lactose, cellulose-lactose complex, pre-gelatinized starch, calcium hydrogen phosphate, calcium carbonate and a combination thereof. The content of the filler is 60%-90%, more preferably 73%-85%, more preferably 73%-82.5% based on the total dry weight of the solid pharmaceutical formulation.

In another preferred example, the filler is microcrystalline cellulose and lactose.

In another preferred example, the solid pharmaceutical formulation further comprises a disintegrant selected from the group consisting of croscarmellose sodium, hypromellose-K4M, crospovidone, sodium carboxymethyl starch and a combination thereof. The content of the disintegrant is 5%-15% based on the total dry weight of the solid pharmaceutical formulation.

In another preferred example, the disintegrant is croscarmellose sodium or hypromellose-K4M.

In another preferred example, the solid pharmaceutical formulation further comprises a lubricant selected from the group consisting of magnesium stearate, talcum powder, glycerol monostearate, sodium stearyl fumarate and a combination thereof. The content of the lubricant is 0.1%-1%, more preferably 0.4%-0.5%, more preferably 0.48%-0.5% based on the total dry weight of the solid pharmaceutical formulation.

In another preferred example, the solid pharmaceutical formulation is a tablet, a capsule, a powder, a granule, a drop pill or a film, preferably a tablet.

In another preferred example, the solid pharmaceutical formulation comprises the following components based on the total dry weight of the solid pharmaceutical formulation:

a) the active ingredient: ((1S,2R,5 S)-2-(((5-fluoropyridin-2-yl)oxy)methyl)-8-azabicyclo[3.2.1]octan-8-yl)(5-methyl-2-(pyrimidin-2-yl)phenyl)methanone, or a pharmaceutically acceptable salt thereof, or a mixture of both, wherein the content of the active ingredient is 1%-15%, more preferably 4%-10%, more preferably 9.5%-10%;

b) the filler selected from the group consisting of microcrystalline cellulose, lactose, cellulose-lactose complex, pre-gelatinized starch, calcium hydrogen phosphate, calcium carbonate and a combination thereof, wherein the content of the filler is 60%-90%, more preferably 73%-85%, more preferably 73%-82.5%;

c) the binder selected from the group consisting of hypromellose, hydroxypropyl cellulose, povidone, sodium alginate, carbopol, polyvinyl alcohol and a combination thereof, wherein the content of the binder is 0.5%-10%, more preferably 1.5%-3%;

d) the disintegrant selected from the group consisting of croscarmellose sodium, hypromellose-K4M, crospovidone, sodium carboxymethyl starch and a combination thereof, wherein the content of the disintegrant is 5%-15%; and e) the lubricant selected from the group consisting of magnesium stearate, talcum powder, glycerol monostearate, sodium stearyl fumarate and a combination thereof, wherein the content of the lubricant is 0.1%-1%, more preferably 0.4%-0.5%, more preferably 0.48%-0.5%;

wherein the particle size of the active ingredient is D90≤35 μm.

In another preferred example, the particle size of the active ingredient is D90≤30 μm. In another preferred example, the particle size of the active ingredient is D90≤20 μm. In another preferred example, the particle size of the active ingredient is D90≤10 μm. In another preferred example, the particle size of the active ingredient is D90=1 μm to 30 μm. In another preferred example, the particle size of the active ingredient is D90=1 μm to 20 μm. In another preferred example, the particle size of the active ingredient is D90=1 μm to 10 μm or D90=10 μm to 20 μm.

In another preferred example, the solid pharmaceutical formulation is a tablet.

In another preferred example, the content of the active ingredient is 5 mg-100 mg. In another preferred example, the content of the active ingredient is 10 mg-50 mg. In another preferred example, the content of the active ingredient is 10 mg, 20 mg or 40 mg.

In another preferred example, the binder is selected from the group consisting of hypromellose-E5, hypromellose-K4M, hypromellose-E50, carbopol, polyvinyl alcohol and a combination thereof.

In another preferred example, the binder is hypromellose-E5.

In another preferred example, the filler is microcrystalline cellulose and lactose.

In another preferred example, the disintegrant is croscarmellose sodium or hypromellose-K4M.

In another preferred example, the solid pharmaceutical formulation comprises the following components based on the total dry weight of the solid pharmaceutical formulation:

a) the active ingredient: ((1S,2R,5S)-2-(((5-fluoropyridin-2-yl)oxy)methyl)-8-azabicyclo[3.2.1]octan-8-yl)(5-methyl-2-(pyrimidin-2-yl)phenyl)methanone, or a pharmaceutically acceptable salt thereof, or a mixture of both, wherein the content of the active ingredient is 4%-10%;
b) the microcrystalline cellulose with a content of 24%-27.5%;
c) the lactose with a content of 48.5%-56.5%;
d) the hypromellose-E5 with a content of 1.5%-3%;
e) the croscarmellose sodium or hypromellose-K4M with a content of 5%-15%; and
f) the magnesium stearate with a content of 0.4%-0.5%;
wherein the particle size of the active ingredient is D90≤35 μm, or D90≤30 μm, or D90≤20 μm, or D90≤10 μm, or D90=1 μm to 30 μm, or D90=1 μm to 20 μm, or D90=1 μm to 10 μm, or D90=10 μm to 20 μm.

In another preferred example, the solid pharmaceutical formulation comprises the following components based on the total dry weight of the solid pharmaceutical formulation:
a) the active ingredient: ((1S,2R,5S)-2-(((5-fluoropyridin-2-yl)oxy)methyl)-8-azabicyclo[3.2.1]octan-8-yl)(5-methyl-2-(pyrimidin-2-yl)phenyl)methanone, or a pharmaceutically acceptable salt thereof, or a mixture of both, wherein the content of the active ingredient is 9.5%-10%;
b) the microcrystalline cellulose with a content of 24%-27.5%;
c) the lactose with a content of 48.5%-56.5%;
d) the hypromellose-E5 with a content of 1.5% to 3%;
e) the croscarmellose sodium or hypromellose-K4M with a content of 5% to 15%; and
f) the magnesium stearate with a content of 0.48% to 0.5%;
wherein the particle size of the active ingredient is D90=1 μm to 30 μm, or D90=1 μm to 20 μm, or D90=1 μm to 10 μm, or D90=10 μm to 20 μm, and the solid pharmaceutical formulation is a tablet.

In another preferred example, the lactose is 200 mesh, 100 mesh, 50 mesh and the like. More preferably, the lactose is 200 mesh.

In another preferred example, the filler is microcrystalline cellulose and lactose. The weight ratio of microcrystalline cellulose to lactose is (24-27.5):(48.5-56.5).

In another preferred example, the solid pharmaceutical formulation comprises any one of tablets in the preparation example.

In another aspect, the present invention provides a unit dosage form, based on a total weight of the unit dosage form, the unit dosage form comprises: about 10 mg, about 20 mg, or about 40 mg of an active ingredient, wherein the active ingredient is a compound of formula (II); about 25 mg to about 150 mg of microcrystalline cellulose (for example, microcrystalline cellulose PH101); about 50 mg to about 300 mg of lactose (for example, Granulac 200); about 1 mg to about 15 mg of hypromellose (for example, hypromellose E5); about 10 mg to about 50 mg of croscarmellose sodium (for example, croscarmellose sodium SD711) or hypromellose (for example, HPMC-K4M); and about 0.5 mg to about 3 mg of magnesium stearate, wherein the particle size of the active ingredient is D90=1 μm to 20 μm. In some embodiments, the particle size of the active ingredient is D90=1 μm to 10 μm or D90=10 μm to 20 μm.

In another aspect, the present invention provides a unit dosage form, based on a total weight of the unit dosage form, the unit dosage form comprises: about 10 mg of an active ingredient, wherein the active ingredient is a compound of formula (II); about 25 mg to about 26 mg of microcrystalline cellulose (for example, microcrystalline cellulose PH101); about 51 mg of lactose (for example, Granulac 200); about 3 mg of hypromellose (for example, hypromellose E5); about 10 mg of croscarmellose sodium (for example, croscarmellose sodium SD711); and about 0.5 mg of magnesium stearate, wherein the particle size of the active ingredient is D90=1 μm to 20 μm. In some embodiments, the particle size of the active ingredient is D90=1 μm to 10 μm or D90=10 μm to 20 μm.

In another aspect, the present invention provides a unit dosage form, based on a total weight of the unit dosage form, the unit dosage form comprises: about 20 mg of an active ingredient, wherein the active ingredient is a compound of formula (II); about 51 mg of microcrystalline cellulose (for example, microcrystalline cellulose PH101); about 102 mg of lactose (for example, Granulac 200); about 6 mg of hypromellose (for example, hypromellose E5); about 20 mg of croscarmellose sodium (for example, croscarmellose sodium SD711); and about 1 mg of magnesium stearate, wherein the particle size of the active ingredient is D90=1 μm to 20 μm. In some embodiments, the particle size of the active ingredient is D90=1 μm to 10 μm or D90=10 μm to 20 μm.

In another aspect, the present invention provides a unit dosage form, based on a total weight of the unit dosage form, the unit dosage form comprises: about 40 mg of an active ingredient, wherein the active ingredient is a compound of formula (II); about 102 mg of microcrystalline cellulose (for example, microcrystalline cellulose PH101); about 204 mg of lactose (for example, Granulac 200); about 12 mg of hypromellose (for example, hypromellose E5); about 40 mg of croscarmellose sodium (for example, croscarmellose sodium SD711); and about 2 mg of magnesium stearate, wherein the particle size of the active ingredient is D90=1 μm to 20 μm. In some embodiments, the particle size of the active ingredient is D90=1 μm to 10 μm or D90=10 μm to 20 μm.

In another aspect, the present invention provides a unit dosage form, based on a total weight of the unit dosage form, the unit dosage form comprises 8 mg to 12 mg of an active ingredient, wherein the active ingredient is a compound of formula (II); 20 mg to 30 mg of microcrystalline cellulose (for example, microcrystalline cellulose PH101); 46 mg to 56 mg of lactose (for example, Granulac 200); 2 mg to 4 mg of hypromellose (for example, hypromellose E5); 5 mg to 15 mg of croscarmellose sodium (for example, croscarmellose sodium SD711); and 0.3 mg to 0.7 mg of magnesium stearate, wherein the particle size of the active ingredient is D90=1 μm to 20 μm. In some embodiments, the particle size of the active ingredient is D90=1 μm to 10 μm or D90=10 μm to 20 μm.

In another aspect, the present invention provides a unit dosage form, based on the total weight of the unit dosage form, the unit dosage form comprises: 18 mg to 22 mg of an active ingredient, wherein the active ingredient is a compound of formula (II); 46 mg to 56 mg of microcrystalline cellulose (for example, microcrystalline cellulose PH101); 97 mg to 107 mg of lactose (for example, Granulac 200); 5 mg to 7 mg of hypromellose (for example, hypromellose E5); 15 mg to 25 mg of croscarmellose sodium (for example, croscarmellose sodium SD711); and 0.8 mg to 1.2 mg of magnesium stearate, wherein the particle size of the active ingredient is D90=1 μm to 20 μm. In some embodiments, the particle size of the active ingredient is D90=1 μm to 10 μm or D90=10 μm to 20 μm.

In another aspect, the present invention provides a unit dosage form, based on a total weight of the unit dosage form, the unit dosage form comprises: 38 mg to 42 mg of an active ingredient, wherein the active ingredient is a compound of formula (II); 97 mg to 107 mg of microcrystalline cellulose (for example, microcrystalline cellulose PH101); 199 mg to 209 mg of lactose (for example, Granulac 200); 11 mg to 13 mg of hypromellose (for example, hypromellose E5); 35 mg to 45 mg of croscarmellose sodium (for example, croscarmellose sodium SD711); and 1.8 mg to 2.2 mg of magnesium stearate, wherein the particle size of the active ingredient is D90=1 μm to 20 μm. In some embodiments, the particle size of the active ingredient is D90=1 μm to 10 μm or D90=10 μm to 20 μm.

In some embodiments, in any one of above unit dosage forms provided by the present invention, the compound of formula (II) as the active ingredient may exist in any form, including amorphous, any crystalline form, hydrate, solvate, and the like. In some embodiments, the compound of formula (II) as the active ingredient exists in amorphous, crystalline form A or crystalline form B. In some embodiments, the compound of formula (II) as the active ingredient exists in crystalline Form A.

In some embodiments, the above unit dosage form is a tablet or a capsule. In some embodiments, the above unit dosage form is a tablet. In some embodiments, the above unit dosage form is a tablet and further comprises a coating.

The tablet can be prepared by methods including conventional compression, wet granulation or dry granulation. In some embodiments, the dosage form of the present invention is a tablet prepared by a wet granulation process. The tablet may also comprise one or more surface coatings, such as a clear coating and/or a colored coating. Various coatings and their application methods are known in the art, including those disclosed in Remington's Pharmaceutical Sciences ($17^{th}$ Edition, Mack Publishing Company, Easton, Pa., 1985). When an appropriate amount of coating is present, the weight of the tablet will usually increase by 2% to 3%, so the weight of the tablet can be generally between about 50 mg and about 1000 mg. In some embodiments, the weight of the tablet is about 100 mg, about 150 mg, about 200 mg, about 250 mg, about 400 mg, about 500 mg, about 600 mg, about 700 mg, about 800 mg, about 900 mg and the like, depending on the dosage required for the therapeutic use.

The expression of "about" used before weight value in the above unit dosage forms of the present invention means a range value of ±10 mg, or ±5 mg, or ±2 mg, or ±1 mg, or ±0.5 mg, or ±0.2 mg, or ±0.1 mg.

The particle size D90 of the active ingredient in the present invention refers to the particle size when the cumulative particle size distribution percentage of a sample reaches 90%.

Film coatings useful in the formulations of the present invention are known in the art and typically comprise polymers (usually cellulosic polymers), colorants and plasticizers. Additional ingredients such as sugars, flavoring agents, oils and lubricants can be comprised in the film coating formulation to impart certain properties to the film coating. The compositions and formulations herein can also be combined and processed into solids and then placed in capsule forms such as gelatin capsules.

It should be understood that some components of the formulations of the present invention may have multiple functions. For example, a given component can be used as a filler or a disintegrant. In some of such cases, the function of the given component may be considered singular, although its properties may allow for multi-functionality.

In the present invention, lactose can be selected from commercially available lactose suitable for the pharmaceutical field, including Flow100, Granulac 200, Tableffose 100, Spherolac 100 and the like. The microcrystalline cellulose can be selected from commercially available microcrystalline cellulose suitable for the pharmaceutical field, including pH101, pH102, pH301, pH302, KG1000, KG802, UF702, UF711 and the like. The pre-gelatinized starch (also known as modified starch) can be selected from commercially available pre-gelatinized starch suitable for the pharmaceutical field, including Starch 1500, PC10 and the like. The hypromellose can be selected from commercially available hypromellose suitable for the pharmaceutical field, including HPMC E3, HPMC E5, HPMC K4M, HPMC E15 and the like. The povidone can be selected from commercially available povidone suitable for the pharmaceutical field, including povidone K30 and povidone K90. The crospovidone can be selected from commercially available crospovidone suitable for the pharmaceutical field, including PVPP XL-10, PVPP VL-10 and PVPP XL. The croscarmellose sodium can be selected from commercially available croscarmellose sodium suitable for the pharmaceutical field, including RC-A591NF, SD-711 and the like.

The second aspect of the present invention provides a method for preparing a tablet, the method comprises the following steps:

(a) performing wet granulation after mixing an active ingredient particle, a filler, a binder and a first disintegrant;
(b) drying a resulting product obtained in step (a);
(c) dry-blending a resulting product obtained in step (b), a second disintegrant and a lubricant; and
(d) compressing a resulting product obtained in step (c) into the tablet;

wherein the active ingredient is ((1S,2R,5S)-2-(((5-fluoropyridin-2-yl)oxy)methyl)-8-azabicyclo[3.2.1]octan-8-yl)(5-methyl-2-(pyrimidin-2-yl)phenyl)methanone, or a pharmaceutically acceptable salt thereof, or a mixture of both;

the particle size of the active ingredient particle is D90≤50 μm.

The first disintegrant and the second disintegrant can be the same or different.

In another preferred example, the particle size of the active ingredient particles is D90≤35 μm. In another preferred example, the particle size of the active ingredient particles is D90≤30 μm. In another preferred example, the particle size of the active ingredient particles is D90≤20 μm. In another preferred example, the particle size of the active ingredient particles is D90≤10 μm. In another preferred example, the particle size of the active ingredient particles is D90=1 μm to 30 μm. In another preferred example, the particle size of the active ingredient particles is D90=1 μm to 20 μm. In another preferred example, the particle size of the active ingredient particles is D90=1 μm to 10 μm. In another preferred example, the particle size of the active ingredient particles is D90=10 μm to 20 μm.

In another preferred example, the filler is selected from the group consisting of microcrystalline cellulose, lactose, cellulose-lactose complex, pre-gelatinized starch, calcium hydrogen phosphate, calcium carbonate and a combination thereof.

In another preferred example, the binder is selected from the group consisting of hypromellose, hydroxypropyl cellulose, povidone, sodium alginate, carbopol, polyvinyl alcohol and a combination thereof.

In another preferred example, the first disintegrant and the second disintegrant are each independently selected from the group consisting of croscarmellose sodium, hypromellose-K4M, crospovidone, sodium carboxymethyl starch and a combination thereof.

In another preferred example, the lubricant is selected from the group consisting of magnesium stearate, talcum powder, glycerol monostearate, sodium stearyl fumarate and a combination thereof.

In another preferred example, based on the total dry weight of the mixture obtained in step (c), the content of the active ingredient is 4%-10%.

In another preferred example, based on the total dry weight of the mixture obtained in step (c), the content of the filler is 73%-82.5%.

In another preferred example, based on the total dry weight of the mixture obtained in step (c), the content of the binder is 1.5%-3%.

In another preferred example, based on the dry weight of all components in step (a), the content of the first disintegrant is 2%-10%, more preferably 5%-6%; based on the dry weight of all components in step (c), the content of the second disintegrant is 5%-10%.

In another preferred example, based on the total dry weight of all components in step (c), the content of the lubricant is 0.1%-1%, more preferably 0.4%-0.5%, more preferably 0.48%-0.5%.

In another preferred example, the method further comprises step (e): coating a product of step (d).

In another preferred example, a coating material in step (e) is a stomach-soluble film coating premix, and the concentration of the coating material is 10%-20%.

In another aspect, the present invention also provides a product prepared by the method described herein.

The third aspect of the present invention provides use of the solid pharmaceutical formulation described in the first aspect of the present invention in the manufacture of a medicament for treating an orexin-associated disease.

More preferably, the orexin-associated diseases include insomnia, chronic obstructive pulmonary disease, obstructive sleep apnea, somnolence, anxiety, obsessive-compulsive disorder, panic, nicotine dependence or eating disorder.

The materials, methods, and examples presented herein are intended to be illustrative, and are not intended to limit the scope of the present invention. All publications, patent applications, patents, and other references mentioned herein are incorporated by reference in their entireties.

It should be understood that, within the scope of the present invention, the above-mentioned technical features of the present invention and the technical features specifically described hereinafter (e.g., the examples) can be combined with each other to form new or preferred technical solutions. For the purpose of brevity, they are not repeated here.

PREPARATION METHOD

Figure 1:
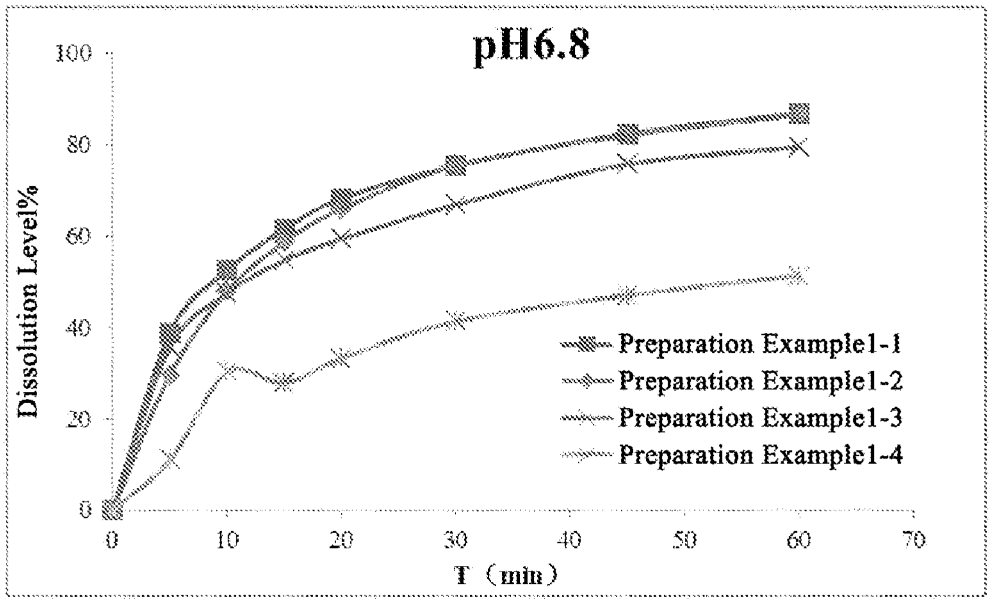
FIG. 1 is a graph showing the dissolution curves of the formulations of Preparation Examples 1-1, 1-2, 1-3 and 1-4.

The solid pharmaceutical formulation of the present invention can be prepared by methods well known in the art. For example, in the case of granule, the compound represented by formula (I) or formula (II) or a pharmaceutically acceptable salt thereof and an excipient, a binder, a disintegrant, a wetting agent and the like can be mixed, and subjected to stirring granulation, extrusion granulation, rotary granulation, one-step spray granulation and the like, or direct dry granulation as required to prepare the granule. In addition, the granule can also be prepared by applying medicine to pellets. In addition, granulation and grinding can also be carried out as required. Furthermore, excipients, disintegrants, binders, antioxidants, colorants and the like can be further added to the above granule for tableting.

For further illustration, the uncoated tablet (plain tablet) or the coated tablet of the present invention can be prepared by the following preparation process by changing the added amount or the corresponding component according to different prescriptions. The preparation process includes: grinding the active pharmaceutical ingredient, sieving the auxiliary material, weighing, mixing and granulating, wet granule sizing, drying, dry granule sizing, final mixing, tableting, and coating (required when preparing a coated tablet).

Grinding the active pharmaceutical ingredient: the particle size of qualified active pharmaceutical ingredient (the compound of formula (I) or formula (II), the pharmaceutically acceptable salt thereof, or the mixture thereof) should be 120-150 μm, which can be achieved by adjusting different parameters of grinding equipment. (1) Particle size control D90≤10 μm, D90≤20 μm or D90≤30 μm: pass the qualified active pharmaceutical ingredient (the compound of formula (I) or formula (II), the pharmaceutically acceptable salt thereof, or the mixture thereof) through a sieve, then add into a jet mill for grinding, control the particle size of the ground active pharmaceutical ingredient by controlling the rotary speed of the feeder at 100 to 500 rpm, adjusting the feed pressure to 3 to 7 bar and the grinding pressure to 2 to 7 bar, and then measure the particle size distribution by a laser particle size distribution analyzer, in which the particle size distribution should meet the particle size D90≤10 μm, D90≤20 μm, or D90≤30 μm; or (2) particle size control D90≤50 μm: taking the qualified active pharmaceutical ingredient (of formula (I) or formula (II)), grinding by a laboratory shear pulverizer, grinding 3 minutes with an interval of 5 minutes, after grinding for a certain period of time, measuring the particle size of the active pharmaceutical ingredient, in which the particle size distribution measured by a laser particle size distribution analyzer should meet D90≤50 μm.

Sieving the auxiliary material: obtain a qualified auxiliary material, lactose (Granulac 200 mesh).

Weighing: weigh the active pharmaceutical ingredient (ground), microcrystalline cellulose (PH101), lactose (Granulac 200 mesh) (sieved), hypromellose-E5, croscarmellose sodium or hypromellose-K4M (with a disintegrant added).

Mixing and granulating: pulping, i.e., binder preparation: weigh 300 g of purified water, add 30 g of hypromellose-E5 while stirring, keep stirring until dissolved to obtain a 10% hypromellose-E5 aqueous solution, pass through a 60-mesh sieve and reserve. Mixing, i.e.: add the active pharmaceutical ingredient (ground) and lactose (sieved) into a wet mixing granulator successively to start stirring and mixing with a stirring speed of 300-500 rpm (for example, 300 rpm or 400 rpm), a chopping speed of 350-400 rpm or 400-500 rpm (for example, 400 rpm), and a stirring time of 300 seconds; open the pot cover, add croscarmellose sodium or hypromellose-K4M (with a disintegrant added), microcrystalline cellulose (PH101) into the pot successively to start stirring and mixing with a stirring speed of 300-500 rpm (for example, 350 rpm or 400 rpm), a chopping speed of 400-500 rpm (preferably 400 rpm), and a stirring time of 600 seconds. Preparing damp mass, the whole process of which is divided into two stages, a first stage: open the wet mixing granulator with pre-set parameters, set the stirring speed to 350-500 rpm (for example, 350 rpm), and the cutting speed to 1000-1500 rpm (for example, 1000 rpm), run for 10 seconds, then slowly add all of 10% (w/w) hypromellose-E5 aqueous binder into the wet mixing granulator, after adding the binder solution, homogenize the obtained wet granules with stirring paddle and chopper until no obvious agglomerates exist, in which the granulation time (slurry adding time) is ≤300 seconds (for example, 60s); and a second stage: set the stirring speed to 500 rpm or 350 rpm, and the cutting speed to 1500 rpm or 1000 rpm, start stirring and cutting at the same time, and continue stirring and cutting for 60s to prepare suitable wet granules.

Wet granule sizing: subject the resulting wet granules to granule sizing by passing through a 18-mesh stainless steel sieve in a swing granule sizing machine or to manually wet granule sizing by passing through a 20-mesh sieve.

Drying: spread the wet granules after granule sizing evenly in a baking tray, in which the thickness of spread wet granules in the tray should be 1.5 cm±0.5 cm, put the baking tray with the spread wet granules into an oven to start drying with a drying temperature of 65.0° C.±5.0° C. Turn the spread wet granules in the tray over and measure the moisture content of the granules for every 30 minutes of drying until the drying end point when the moisture content of the granules after drying 2.0%.

Dry granule sizing: subject the dried granules to granule sizing by passing through a 20-mesh stainless steel sieve in a swing granule sizing machine.

Final mixing: add croscarmellose sodium or hypromellose-K4M (with a disintegrant added), the granules after dry granule sizing and magnesium stearate into a mixer at the same time and mix for 300 seconds with a mixing speed of 16 rpm. After final mixing, the total moisture content of the granules should be 3.0%.

Tableting: obtain the final mixed granules of the active pharmaceutical ingredient, and subject to tableting by a rotary tableting machine.

Coating: coat the plain tablets obtained by tableting to obtain a desired coating weight gain of 2% to 3%. The stomach-soluble film coating premix is selected as the coating material, and the concentration of the coating solution is 15%. The specific preparation method comprises: taking 30 g of coating powder, adding into 200 g of purified water, and stirring to disperse evenly to obtain the coating solution (formulated according to 200% of the weight gain at 3%), and then coating the tablets by a high-efficiency coater. Coating can be carried out by using the following process parameters.

| | |
|---|---|
| Inlet air temperature (° C.) | 55.0-65.0 |
| Outlet air temperature (° C.) | 45.0-50.0 |
| Heating (° C.) | 70.0-75.0 |
| Air volume ($m^3$/h) | 80.0-85.0 |
| Flow rate (g/min) | 85-90 |
| Main engine rotary speed (rpm) | 3.0-5.5 |
| Spray gun pressure (bar) | 0.11 or 0.9 |

DETAILED DESCRIPTION OF THE INVENTION

The present invention will be further described below in conjunction with specific examples. It should be understood that these examples are only used to illustrate the present invention and are not intended to limit the scope of the present invention. In the following examples, the experimental methods without specific conditions are usually in accordance with conventional conditions, or in accordance with the conditions suggested by the manufacturer. Percentages and parts are weight percentages and weight parts unless otherwise specified. The experimental materials and reagents used in the following examples can be obtained from commercial sources unless otherwise specified.

The single crystal structure is tested using a D8 Venture X-ray single crystal diffractometer, light source: Cu target, X-ray: Cu-Kα (=1.54178 Å), detector: CMOS surface detector, resolution: 0.8 Å, current and voltage: 50 kV, 1.2 mA, exposure time: 10s, distance from the surface detector to the sample: 40 mm, test temperature: 150(2)K.

Unless otherwise stated, the weight percentages set forth for the active ingredient, the filler component, the binder component, the disintegrant component, and the lubricant component of the solid pharmaceutical formulation disclosed herein are the percentage of each component in the final solid pharmaceutical formulation without any surface coverings, such as a tablet coating (e.g., any clear coating or colored coating) or a capsule. The calculation of the weight percentages of the active ingredient, the filler component, the binder component, the disintegrant component and the lubricant component may slightly change, since the coated tablet in the following specific examples include the weight of the coating. However, the following examples are only used to illustrate the present invention and are not intended to limit the scope of the present invention. Unless otherwise stated, the active ingredient of the compound of formula (II) exists in crystalline form A, the microcrystalline cellulose is microcrystalline cellulose PH101, the lactose is lactose Granulac 200 mesh, and the croscarmellose sodium is croscarmellose sodium SD711 in the specific formulations in the following preparation examples.

Preparation Example 1-1 Uncoated Plain Tablet Formulation

Tablet formulation comprising the compound of formula (II) (mass percent):

| | |
|---|---|
| compound of formula (II) | 4% |
| microcrystalline cellulose | 26.16% |
| lactose | 56.32% |
| hypromellose-E5 | 3.04% |
| croscarmellose sodium | 10% |
| magnesium stearate | 0.48% |

The compound of formula (II) was passed through a 20-mesh sieve, and then the sieved active pharmaceutical ingredient was added into a jet mill and ground under the grinding pressure of 6 to 7 bar, the inlet pressure of 7 to 8 bar, the feed pressure of 6 to 7 bar, and the feed rotary speed of 100 to 150 rpm. After the grinding was completed, samples were taken and tested, and the particle size distribution was measured by a laser particle size distribution analyzer, showing the particle size D90≤10 μm (D90=7.461 μm). The compound of formula (II) with the particle size of D90≤10 μm (D90=7.461 μm) and lactose were added into a wet mixing granulator, stirred and mixed, and then microcrystalline cellulose and croscarmellose sodium were added, stirred and mixed. Then 10% (mass percent) hypromellose-E5 aqueous solution was slowly added into the wet mixing granulator for performing wet granulation. The resultant was subjected to wet granule sizing and dried in an oven. The moisture content of the dried granules was ≤2.0%. Then dry granule sizing was performed. The resulting granules after dry granule sizing, croscarmellose sodium and magnesium stearate were finally mixed in a mixer. The total moisture content of the granules after final mixing was ≤3.0%. The granules were tableted to prepare uncoated plain tablets having a specification of 500 mg.

Preparation Example 1-2 Uncoated Plain Tablet Formulation

Tablet formulation comprising the compound of formula (II) (mass percent):

| | |
|---|---|
| compound of formula (II) | 4% |
| microcrystalline cellulose | 26.16% |
| lactose | 56.32% |
| hypromellose-E5 | 3.04% |
| croscarmellose sodium | 10% |
| magnesium stearate | 0.48% |

The compound of formula (II) was passed through a 20-mesh sieve, and then the sieved active pharmaceutical ingredient was added into a jet mill and ground under the grinding pressure of 4 to 6 bar, the inlet pressure of 6 to 7 bar, the feed pressure of 5 to 6 bar, and the feed rotary speed of 200 to 300 rpm. Samples were taken and tested, and the particle size distribution was measured by a laser particle size distribution analyzer, showing the particle size D90≤20 μm (D90=17.89 μm). The compound of formula (II) with D90≤20 μm (D90=17.89 μm) and lactose were added into a wet mixing granulator, stirred and mixed, and then microcrystalline cellulose and croscarmellose sodium were added, stirred and mixed. Then 10% (mass percent) hypromellose-E5 aqueous solution was slowly added into the wet mixing granulator for performing wet granulation. The resultant was subjected to wet granule sizing and dried in an oven. The moisture content of the dried granules was ≤2.0%. Then dry granule sizing was performed. The resulting granules after dry granule sizing, croscarmellose sodium and magnesium stearate were finally mixed in a mixer. The total moisture content of the granules after final mixing was 3.0%. The granules were tableted to prepare uncoated plain tablets having a specification of 500 mg.

Preparation Example 1-3 Uncoated Plain Tablet Formulation

Tablet formulation comprising the compound of formula (II) (mass percent):

| | |
|---|---|
| compound of formula (II) | 4% |
| microcrystalline cellulose | 26.16% |
| lactose | 56.32% |
| hypromellose-E5 | 3.04% |
| croscarmellose sodium | 10% |
| magnesium stearate | 0.48% |

The compound of formula (II) was passed through a 20-mesh sieve, and then the sieved active pharmaceutical ingredient was added into a jet mill and ground under the grinding pressure of 2 to 4 bar, the inlet pressure of 4 to 5 bar, the feed pressure of 3 to 4 bar, and the feed rotary speed of 300 to 400 rpm. After the grinding was completed, samples were taken and tested, and the particle size distribution was measured by a laser particle size distribution analyzer, showing the particle size D90≤35 μm (D90=30.7 μm). The compound of formula (II) with D90≤35 μm (D90=30.7 μm) and lactose were added into a wet mixing granulator, stirred and mixed, and then microcrystalline cellulose and croscarmellose sodium were added, stirred and mixed. Then 10% (mass percent) hypromellose-E5 aqueous solution was slowly added into the wet mixing granulator for performing wet granulation. The resultant was subjected to wet granule sizing and dried in an oven. The moisture content of the dried granules was ≤2.0%. Then dry granule sizing was performed. The resulting granules after dry granule sizing, croscarmellose sodium and magnesium stearate were finally mixed in a mixer. The total moisture content of the granules after final mixing was ≤3.0%. The granules were tableted to prepare uncoated plain tablets having a specification of 500 mg.

Preparation Example 1-4 Uncoated Plain Tablet Formulation

Tablet formulation comprising the compound of formula (II) (mass percent):

| | |
|---|---|
| compound of formula (II) | 4% |
| microcrystalline cellulose | 26.16% |
| lactose | 56.32% |
| hypromellose-E5 | 3.04% |
| croscarmellose sodium | 10% |
| magnesium stearate | 0.48% |

After the compound of formula (II) was passed through a 20-mesh sieve, the particle size distribution was measured by a laser particle size distribution analyzer, showing the particle size D90≤150 μm (D90=144.5 μm). The compound of formula (II) with the particle size of D90≤150 μm (D90=144.5 μm) and lactose were added into a wet mixing granulator, stirred and mixed, and then microcrystalline cellulose and croscarmellose sodium were added, stirred and mixed. Then 10% (mass percent) hypromellose-E5 aqueous solution was slowly added into the wet mixing granulator for performing wet granulation. The resultant was subjected to wet granule sizing and dried in an oven. The moisture content of the dried granules was 2.0%. Then dry granule sizing was performed. The resulting granules after dry granule sizing, croscarmellose sodium and magnesium stearate were finally mixed in a mixer. The total moisture content of the granules after final mixing was 3.0%. The granules were tableted to prepare uncoated plain tablets having a specification of 500 mg.

Preparation Example 2-1 Coated Tablet Formulation

Tablet formulation comprising the compound of formula (II) (mass percent):

| | |
|---|---|
| compound of formula (II) | 9.76% |
| microcrystalline cellulose | 24.88% |
| lactose | 49.76% |
| hypromellose-E5 | 2.93% |
| croscarmellose sodium | 9.76% |
| magnesium stearate | 0.49% |
| film coating premix | 2.44% |

The compound of formula (II) was passed through a 20-mesh sieve, and then the sieved active pharmaceutical ingredient was added into a jet mill and ground under the grinding pressure of 4 to 6 bar, the inlet pressure of 6 to 7 bar, the feed pressure of 5 to 6 bar, and the feed rotary speed of 200 to 300 rpm. Samples were taken and tested, and the particle size distribution was measured by a laser particle size distribution analyzer, showing the particle size D90≤20 μm (D90=17.89 μm). The compound of formula (II) with the particle size of D90≤20 μm (D90=17.89 μm) and lactose were added into a wet mixing granulator, stirred and mixed, and then microcrystalline cellulose and croscarmellose sodium were added, stirred and mixed. Then 10% (mass percent) hypromellose-E5 aqueous solution was slowly added into the wet mixing granulator for performing wet granulation. The resultant was subjected to wet granule sizing and dried in an oven. The moisture content of the dried granules was ≤2.0%. Then dry granule sizing was performed. The resulting granules after dry granule sizing, croscarmellose sodium and magnesium stearate were finally mixed in a mixer. The total moisture content of the granules after final mixing was ≤3.0%. The granules were tableted and coated with a stomach-soluble film coating premix to prepare tablets having a specification of 205 mg.

Preparation Example 2-2 Coated Tablet Formulation

Tablet formulation comprising the compound of formula (II) (mass percent):

| | |
|---|---|
| compound of formula (II) | 9.76% |
| microcrystalline cellulose | 24.88% |
| lactose | 49.76% |
| hypromellose-E5 | 2.93% |
| croscarmellose sodium | 9.76% |
| magnesium stearate | 0.49% |
| film coating premix | 2.44% |

The compound of formula (II) was passed through a 20-mesh sieve, and then the sieved active pharmaceutical ingredient was added into a jet mill and ground under the grinding pressure of 4 to 6 bar, the inlet pressure of 6 to 7 bar, the feed pressure of 5 to 6 bar, and the feed rotary speed of 200 to 300 rpm. Samples were taken and tested, and the particle size distribution was measured by a laser particle size distribution analyzer, showing the particle size D90≤20 μm (D90=17.89 μm). The compound of formula (II) with D90≤20 μm (D90=17.89 μm) and lactose were added into a wet mixing granulator, stirred and mixed, and then microcrystalline cellulose and croscarmellose sodium were added, stirred and mixed. Then 10% (mass percent) hypromellose-E5 aqueous solution was slowly added into the wet mixing granulator for performing wet granulation. The resultant was subjected to wet granule sizing and dried in an oven. The moisture content of the dried granules was ≤2.0%. Then dry granule sizing was performed. The resulting granules after dry granule sizing, croscarmellose sodium and magnesium stearate were finally mixed in a mixer. The total moisture content of the granules after final mixing was ≤3.0%. The granules were tableted and coated with a stomach-soluble film coating premix to prepare tablets having a specification of 410 mg.

Preparation Example 2-3 Coated Tablet Formulation

Tablet formulation comprising the compound of formula (II) (mass percent):

| | |
|---|---|
| compound of formula (II) | 9.76% |
| microcrystalline cellulose | 24.88% |
| lactose | 49.76% |
| hypromellose-E5 | 2.93% |
| croscarmellose sodium | 9.76% |
| magnesium stearate | 0.49% |
| film coating premix | 2.44% |

The compound of formula (II) was passed through a 20-mesh sieve, and then the sieved active pharmaceutical ingredient was added into a jet mill and ground under the grinding pressure of 6 to 7 bar, the inlet pressure of 7 to 8 bar, the feed pressure of 6 to 7 bar, and the feed rotary speed of 100 to 150 rpm. After the grinding was completed, samples were taken and tested, and the particle size distribution was measured by a laser particle size distribution analyzer, showing the particle size D90≤10 μm (D90=7.461 μm). The compound of formula (II) with the particle size of D90≤10 μm (D90=7.461 μm) and lactose were added into a wet mixing granulator, stirred and mixed, and then microcrystalline cellulose and croscarmellose sodium were added, stirred and mixed. Then 10% (mass percent) hypromellose-E5 aqueous solution was slowly added into the wet mixing granulator for performing wet granulation. The resultant was subjected to wet granule sizing and dried in an oven. The moisture content of the dried granules was ≤2.0%. Then dry granule sizing was performed. The resulting granules after dry granule sizing, croscarmellose sodium and magnesium stearate were finally mixed in a mixer. The total moisture content of the granules after final mixing was ≤3.0%. The granules were tableted and coated with a stomach-soluble film coating premix to prepare tablets having a specification of 205 mg.

Preparation Example 2-4 Coated Tablet Formulation

Tablet formulation comprising the compound of formula (II) (mass percent):

| | |
|---|---|
| compound of formula (II) | 9.76% |
| microcrystalline cellulose | 24.88% |
| lactose | 49.76% |
| hypromellose-E5 | 2.93% |
| croscarmellose sodium | 9.76% |
| magnesium stearate | 0.49% |
| film coating premix | 2.44% |

The compound of formula (II) was passed through a 20-mesh sieve, and ground by a laboratory shear pulverizer, grinding 3 minutes with an interval of 5 minutes. After grinding for 10 minutes, the particle size distribution was measured by a laser particle size distribution analyzer, showing the particle size D90≤50 μm (D90=45.71 μm). The compound of formula (II) with the particle size of D90≤50 μm (D90=45.71 μm) and lactose were added into a wet mixing granulator, stirred and mixed, and then microcrystalline cellulose and croscarmellose sodium were added, stirred and mixed. Then 10% (mass percent) hypromellose-E5 aqueous solution was slowly added into the wet mixing granulator for performing wet granulation. The resultant was subjected to wet granule sizing and dried in an oven. The moisture content of the dried granules was ≤2.0%. Then dry granule sizing was performed. The resulting granules after dry granule sizing, croscarmellose sodium and magnesium stearate were finally mixed in a mixer. The total moisture content of the granules after final mixing was ≤3.0%. The granules were tableted and coated with a stomach-soluble film coating premix to prepare tablets having a specification of 205 mg.

Preparation Example 2-5 Coated Tablet Formulation

Tablet formulation comprising the compound of formula (II) (mass percent):

| | |
|---|---|
| compound of formula (II) | 9.76% |
| microcrystalline cellulose | 24.88% |
| lactose | 49.76% |
| hypromellose-E5 | 2.93% |
| croscarmellose sodium | 9.76% |
| magnesium stearate | 0.49% |
| film coating premix | 2.44% |

After the compound of formula (II) was passed through a 20-mesh sieve, the particle size distribution was measured by a laser particle size distribution analyzer, showing the particle size D90≤150 μm (D90=144.5 μm). The compound of formula (II) with the particle size of D90≤150 μm (D90=144.5 μm) and lactose were added into a wet mixing granulator, stirred and mixed, and then microcrystalline cellulose and croscarmellose sodium were added, stirred and mixed. Then 10% (mass percent) hypromellose-E5 aqueous solution was slowly added into the wet mixing granulator for performing wet granulation. The resultant was subjected to wet granule sizing and dried in an oven. The moisture content of the dried granules was ≤2.0%. Then dry granule sizing was performed. The resulting granules after dry granule sizing, croscarmellose sodium and magnesium stearate were finally mixed in a mixer. The total moisture content of the granules after final mixing was ≤3.0%. The granules were tableted and coated with a stomach-soluble film coating premix to prepare tablets having a specification of 205 mg.

Preparation Example 2-6 Uncoated Plain Tablet Formulation

Tablet formulation comprising the compound of formula (II) (mass percent):

| | |
|---|---|
| compound of formula (II) | 10% |
| microcrystalline cellulose | 25.5% |
| lactose | 51% |
| hypromellose-E5 | 3% |
| croscarmellose sodium | 10% |
| magnesium stearate | 0.5% |

The compound of formula (II) was passed through a 20-mesh sieve, and then the sieved active pharmaceutical ingredient was added into a jet mill and ground under the grinding pressure of 4 to 6 bar, the inlet pressure of 6 to 7 bar, the feed pressure of 5 to 6 bar, and the feed rotary speed of 200 to 300 rpm. Samples were taken and tested, and the particle size distribution was measured by a laser particle size distribution analyzer, showing the particle size D90≤20 μm (D90=17.89 μm). The compound of formula (II) with the particle size of D90≤20 μm (D90=17.89 μm) and lactose were added into a wet mixing granulator, stirred and mixed, and then microcrystalline cellulose and croscarmellose sodium were added, stirred and mixed. Then 10% (mass percent) hypromellose-E5 aqueous solution was slowly added into the wet mixing granulator for performing wet granulation. The resultant was subjected to wet granule sizing and dried in an oven. The moisture content of the dried granules was ≤2.0%. Then dry granule sizing was performed. The resulting granules after dry granule sizing, croscarmellose sodium and magnesium stearate were finally mixed in a mixer. The total moisture content of the granules after final mixing was ≤3.0%. The granules were tableted to prepare uncoated tablets having a specification of 200 mg.

Preparation Example 2-7 Uncoated Plain Tablet Formulation

Tablet formulation comprising the compound of formula (II) (mass percent):

| | |
|---|---|
| compound of formula (II) | 10% |
| microcrystalline cellulose | 25.5% |
| lactose | 51% |
| hypromellose-E5 | 3% |
| croscarmellose sodium | 10% |
| magnesium stearate | 0.5% |

The compound of formula (II) was passed through a 20-mesh sieve, and then the sieved active pharmaceutical ingredient was added into a jet mill and ground under the grinding pressure of 4 to 6 bar, the inlet pressure of 6 to 7 bar, the feed pressure of 5 to 6 bar, and the feed rotary speed of 200 to 300 rpm. Samples were taken and tested, and the particle size distribution was measured by a laser particle size distribution analyzer, showing the particle size D90≤20 μm (D90=17.89 μm). The compound of formula (II) with the particle size of D90≤20 μm (D90=17.89 μm) and lactose were added, stirred and mixed, and then microcrystalline cellulose and croscarmellose sodium were added, stirred and mixed. Then 10% (mass percent) hypromellose-E5 aqueous solution was slowly added into the wet mixing granulator for performing wet granulation. The resultant was subjected to wet granule sizing and dried in an oven. The moisture content of the dried granules was ≤2.0%. Then dry granule sizing was performed. The resulting granules after dry granule sizing, croscarmellose sodium and magnesium stearate were finally mixed in a mixer. The total moisture content of the granules after final mixing was 3.0%. The granules were tableted to prepare uncoated plain tablets having a specification of 400 mg.

Preparation Example 2-8 Coated Tablet Formulation

Tablet formulation comprising the compound of formula (II) (mass percent):

| | |
|---|---|
| compound of formula (II) | 9.76% |
| microcrystalline cellulose | 24.88% |
| lactose | 49.76% |
| hypromellose-E5 | 2.93% |
| croscarmellose sodium | 9.76% |
| magnesium stearate | 0.49% |
| film coating premix | 2.44% |

The compound of formula (II) was passed through a 20-mesh sieve, and then the sieved active pharmaceutical ingredient was added into a jet mill and ground under the grinding pressure of 6 to 7 bar, the inlet pressure of 7 to 8 bar, the feed pressure of 6 to 7 bar, and the feed rotary speed of 100 to 150 rpm. After the grinding was completed, samples were taken and tested, and the particle size distribution was measured by a laser particle size distribution analyzer, showing the particle size D90≤10 μm (D90=8.93 μm). The compound of formula (II) with the particle size of D90≤10 μm (D90=8.93 μm) and lactose were added into a wet mixing granulator, stirred and mixed, and then microcrystalline cellulose and croscarmellose sodium were added, stirred and mixed. Then 10% (mass percent) hypromellose-E5 aqueous solution was slowly added into the wet mixing granulator for performing wet granulation. The resultant was subjected to wet granule sizing and dried in an oven. The moisture content of the dried granules was ≤2.0%. Then dry granule sizing was performed. The resulting granules after dry granule sizing, croscarmellose sodium and magnesium stearate were finally mixed in a mixer. The total moisture content of the granules after final mixing was ≤3.0%. The granules were tableted and coated with a stomach-soluble film coating premix to prepare tablets having a specification of 205 mg.

Preparation Example 3 Uncoated Plain Tablet Formulation

Tablet formulation comprising the compound of formula (II) (mass percent):

| | |
|---|---|
| compound of formula (II) | 4% |
| microcrystalline cellulose | 26.2% |
| lactose | 56.3% |
| hypromellose-E5 | 3% |
| croscarmellose sodium | 10% |
| magnesium stearate | 0.48% |

The compound of formula (II) was passed through a 20-mesh sieve, and then the sieved active pharmaceutical ingredient was added into a jet mill and ground under the grinding pressure of 6 to 7 bar, the inlet pressure of 7 to 8 bar, the feed pressure of 6 to 7 bar, and the feed rotary speed of 100 to 150 rpm. After the grinding was completed, samples were taken and tested, and the particle size distribution was measured by a laser particle size distribution analyzer, showing the particle size D90≤10 μm (D90=7.461 μm). The compound of formula (II) with the particle size of D90≤10 μm (D90=7.461 μm), lactose, and microcrystalline cellulose were added into a wet mixing granulator, stirred and mixed. Then 10% (mass percent) hypromellose-E5 aqueous solution was slowly added for performing wet granulation. The resultant was subjected to wet granule sizing and dried in an oven. The moisture content of the dried granules was ≤2.0%. Then dry granule sizing was performed. The resulting granules after dry granule sizing, croscarmellose sodium and magnesium stearate were finally mixed in a mixer. The total moisture content of the granules after final mixing was ≤3.0%. The granules were tableted to prepare tablets having a specification of 500 mg.

Preparation Example 4-1 Uncoated Plain Tablet Formulation

Tablet formulation comprising the compound of formula (II) (mass percent):

| | |
|---|---|
| compound of formula (II) | 10% |
| microcrystalline cellulose | 24.3% |
| lactose | 48.7% |
| hypromellose-E5 | 1.5% |
| hypromellose-K4M | 15% |
| magnesium stearate | 0.5% |

The compound of formula (II) was passed through a 20-mesh sieve, and then the sieved active pharmaceutical ingredient was added into a jet mill and ground under the grinding pressure of 4 to 6 bar, the inlet pressure of 6 to 7 bar, the feed pressure of 5 to 6 bar, and the feed rotary speed of 200 to 300 rpm. Samples were taken and tested, and the particle size distribution was measured by a laser particle size distribution analyzer, showing the particle size D90≤20 μm (D90=17.89 μm). The compound of formula (II) with D90≤20 μm (D90=17.89 μm), lactose, microcrystalline cellulose and hypromellose-K4M were added into a wet mixing granulator, stirred and mixed. Then 10% (mass percent) hypromellose-E5 aqueous solution was slowly added for performing wet granulation. The resultant was subjected to wet granule sizing and dried in an oven. The moisture content of the dried granules was ≤2.0%. Then dry granule sizing was performed. The resulting granules after dry granule sizing, hypromellose-K4M and magnesium stearate were finally mixed in a mixer. The total moisture content of the granules after final mixing was ≤3.0%. The granules were tableted to prepare tablets having a specification of 200 mg.

Preparation Example 4-2 Uncoated Plain Tablet Formulation

Tablet formulation comprising the compound of formula (II) (mass percent):

| | |
|---|---|
| compound of formula (II) | 10% |
| microcrystalline cellulose | 27.5% |
| lactose | 55% |
| hypromellose-E5 | 2% |
| hypromellose-K4M | 5% |
| magnesium stearate | 0.5% |

The compound of formula (II) was passed through a 20-mesh sieve, and then the sieved active pharmaceutical ingredient was added into a jet mill and ground under the grinding pressure of 4 to 6 bar, the inlet pressure of 6 to 7 bar, the feed pressure of 5 to 6 bar, and the feed rotary speed of 200 to 300 rpm. Samples were taken and tested, and the particle size distribution was measured by a laser particle size distribution analyzer, showing the particle size D90≤20 μm (D90=17.89 μm). The compound of formula (II) with D90≤20 μm (D90=17.89 μm), lactose, microcrystalline cellulose and hypromellose-K4M were added into a wet mixing granulator, stirred and mixed. Then 10% (mass percent) hypromellose-E5 aqueous solution was slowly added for performing wet granulation. The resultant was subjected to wet granule sizing and dried in an oven. The moisture content of the dried granules was ≤2.0%. Then dry granule sizing was performed, and the resulting granules after dry granule sizing, hypromellose-K4M and magnesium stearate were finally mixed in a mixer. The total moisture content of the granules after final mixing was ≤3.0%. The granules were tableted to prepare tablets having a specification of 200 mg.

Preparation Example 4-3 Uncoated Plain Tablet Formulation

Tablet formulation comprising the compound of formula (II) (mass percent):

| | |
|---|---|
| compound of formula (II) | 10% |
| microcrystalline cellulose | 25.8% |
| lactose | 51.7% |
| hypromellose-E5 | 2% |
| hypromellose-K4M | 10% |
| magnesium stearate | 0.5% |

The compound of formula (II) was passed through a 20-mesh sieve, and then the sieved active pharmaceutical ingredient was added into a jet mill and ground under the grinding pressure of 4 to 6 bar, the inlet pressure of 6 to 7 bar, the feed pressure of 5 to 6 bar, and the feed rotary speed of 200 to 300 rpm. Samples were taken and tested, and the particle size distribution was measured by a laser particle size distribution analyzer, showing the particle size D90≤20 μm (D90=17.89 μm). The compound of formula (II) with D90≤20 μm (D90=17.89 μm), lactose, microcrystalline cellulose and hypromellose-K4M were added into a wet mixing granulator, stirred and mixed. Then 10% (mass percent) hypromellose-E5 aqueous solution was slowly added for performing wet granulation. The resultant was subjected to wet granule sizing and dried in an oven. The moisture content of the dried granules was ≤2.0%. Then dry granule sizing was performed, and the resulting granules after dry granule sizing, hypromellose-K4M and magnesium stearate were finally mixed in a mixer. The total moisture content of the granules after final mixing was ≤3.0%. The granules were tableted to prepare tablets having a specification of 200 mg.

Preparation Example 5 Coated Tablet Formulation

Tablet formulation comprising the compound of formula (II) (mass percent):

| | |
|---|---|
| compound of formula (II) | 9.8% |
| microcrystalline cellulose | 25% |
| lactose | 50% |
| hypromellose-E5 | 2.94% |
| croscarmellose sodium | 9.8% |
| magnesium stearate | 0.49% |
| film coating premix | 1.96% |

The compound of formula (II) was passed through a 20-mesh sieve, and then the sieved active pharmaceutical ingredient was added into a jet mill and ground under the grinding pressure of 4 to 6 bar, the inlet pressure of 6 to 7 bar, the feed pressure of 5 to 6 bar, and the feed rotary speed of 200 to 300 rpm. Samples were taken and tested, and the particle size distribution was measured by a laser particle size distribution analyzer, showing the particle size D90≤20 μm (D90=17.89 μm). The compound of formula (II) with D90≤20 μm (D90=17.89 μm) and lactose were added into a wet mixing granulator, stirred and mixed, and then microcrystalline cellulose and croscarmellose sodium were added, stirred and mixed. Then 10% (mass percent) hypromellose-E5 aqueous solution was slowly added into the wet mixing granulator for performing wet granulation. The resultant was subjected to wet granule sizing and dried in an oven. The moisture content of the dried granules was ≤2.0%. Then dry granule sizing was performed. The resulting dry granules, croscarmellose sodium and magnesium stearate were finally mixed in a mixer. The total moisture content of the granules after final mixing was ≤3.0%. The granules were tableted and coated with a stomach-soluble film coating premix to prepare tablets having a specification of 102 mg.

Preparation Example 6 Coated Tablet Formulation

Tablet formulation comprising the compound of formula (II) (mass percent):

| | |
|---|---|
| compound of formula (II) | 9.76% |
| microcrystalline cellulose | 24.88% |
| lactose | 49.76% |
| hypromellose-E5 | 2.93% |
| croscarmellose sodium | 9.76% |
| magnesium stearate | 0.49% |
| film coating premix | 2.44% |

The compound of formula (II) (in crystalline form B) was passed through a 20-mesh sieve, and then the sieved active pharmaceutical ingredient was added into a jet mill and ground under the grinding pressure of 6 to 7 bar, the inlet pressure of 7 to 8 bar, the feed pressure of 6 to 7 bar, and the feed rotary speed of 100 to 150 rpm. Samples was taken and tested, and the particle size distribution was measured by a laser particle size distribution analyzer, showing the particle size D90≤20 μm (D90=10.09 μm). The compound of formula (II) with the particle size of D90≤20 μm (D90=10.09 μm) and lactose were added into a wet mixing granulator, stirred and mixed, and then microcrystalline cellulose and croscarmellose sodium were added, stirred and mixed. Then 10% (mass percent) hypromellose-E5 aqueous solution was slowly added into the wet mixing granulator for performing wet granulation. The resultant was subjected to wet granule sizing and dried in an oven. The moisture content of the dried granules was ≤2.0%. Then dry granule sizing was performed. The resulting granules after dry granule sizing, croscarmellose sodium and magnesium stearate were finally mixed in a mixer, the total moisture content of the granules after final mixing was ≤3.0%. The granules were tableted and coated with a stomach-soluble film coating premix to prepare tablets having a specification of 205 mg.

Test Example 1 In Vitro Dissolution Test

Figure 2:
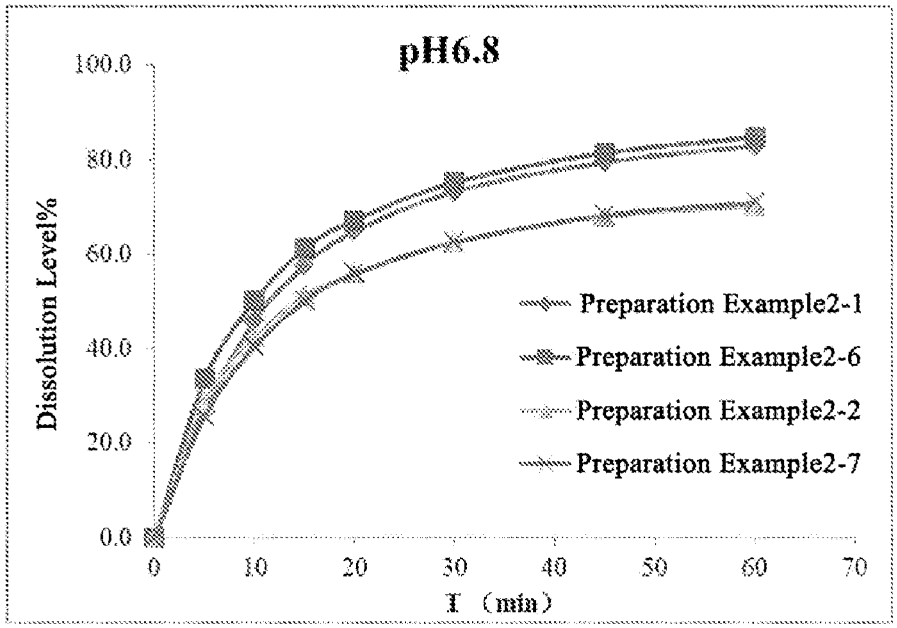
FIG. 2 is a graph showing the dissolution curves of the formulations of Preparation Examples 2-1, 2-2, 2-6 and 2-7.
Figure 3:
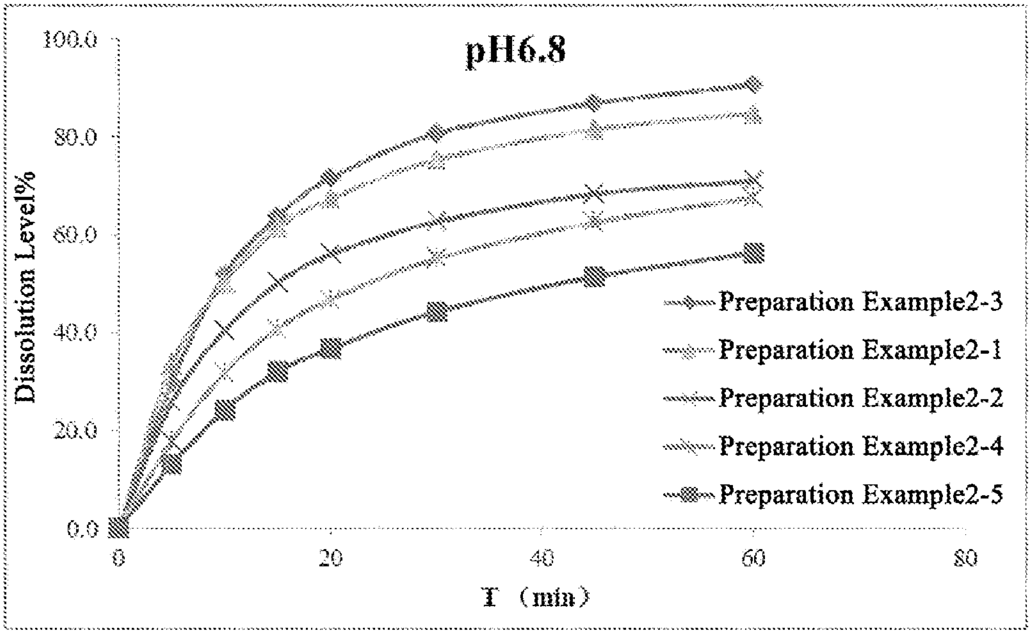
FIG. 3 is a graph showing the dissolution curves of the formulations of Preparation Examples 2-1, 2-2, 2-3, 2-4 and 2-5.
Figure 4:
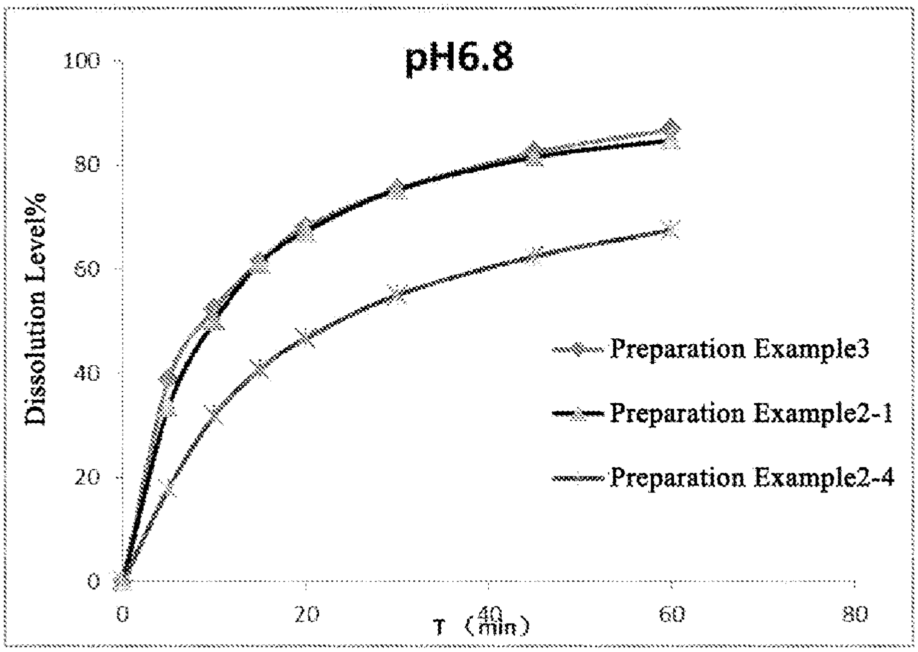
FIG. 4 is a graph showing the dissolution curves of the formulations of Preparation Examples 3, 2-1 and 2-4.
Figure 5:
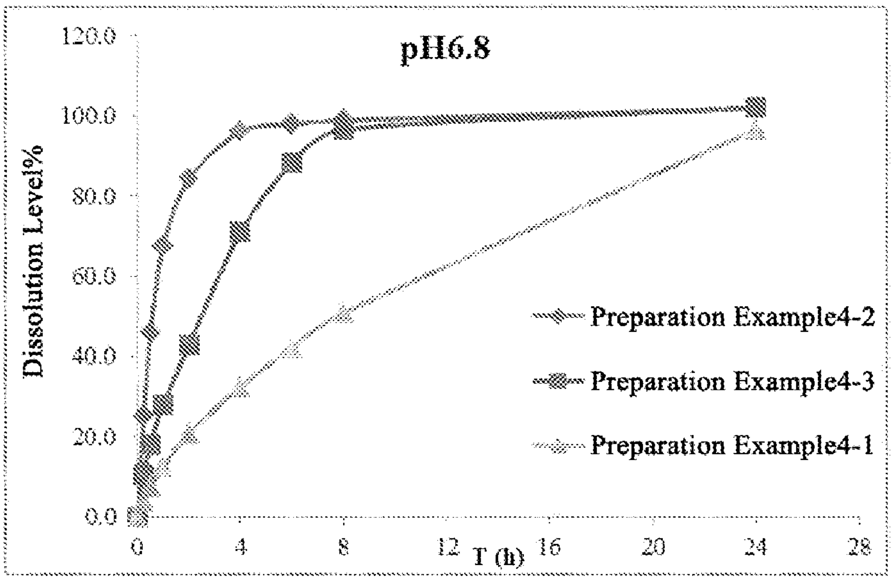
FIG. 5 is a graph showing the dissolution curves of the formulations of Preparation Examples 4-1, 4-2 and 4-3.
Figure 6:
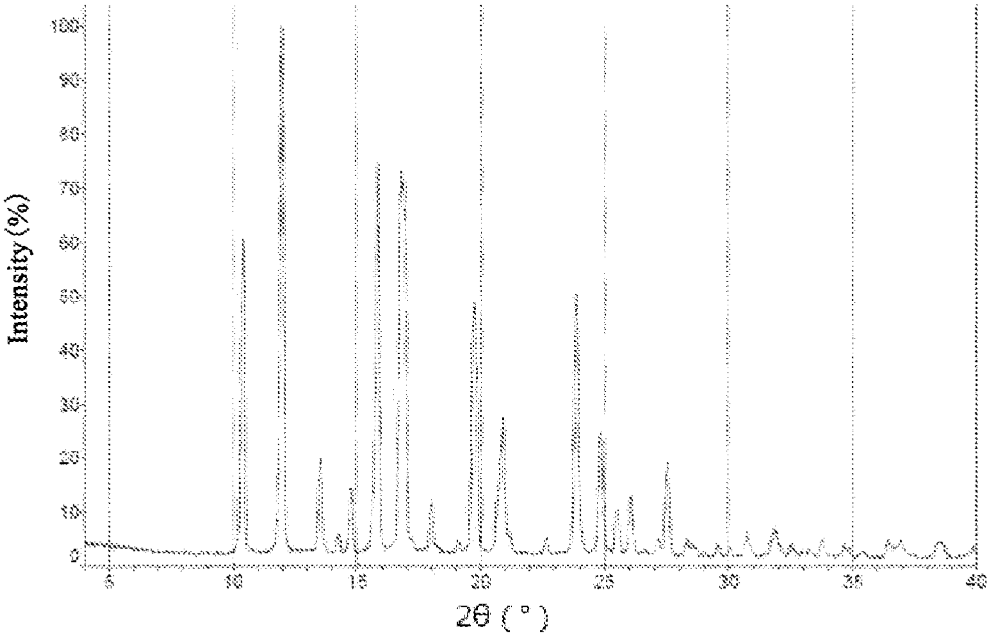
FIG. 6 is an XRPD spectrum using Cu-Kα radiation of the compound of formula (II) in crystalline form A.
Figure 7:
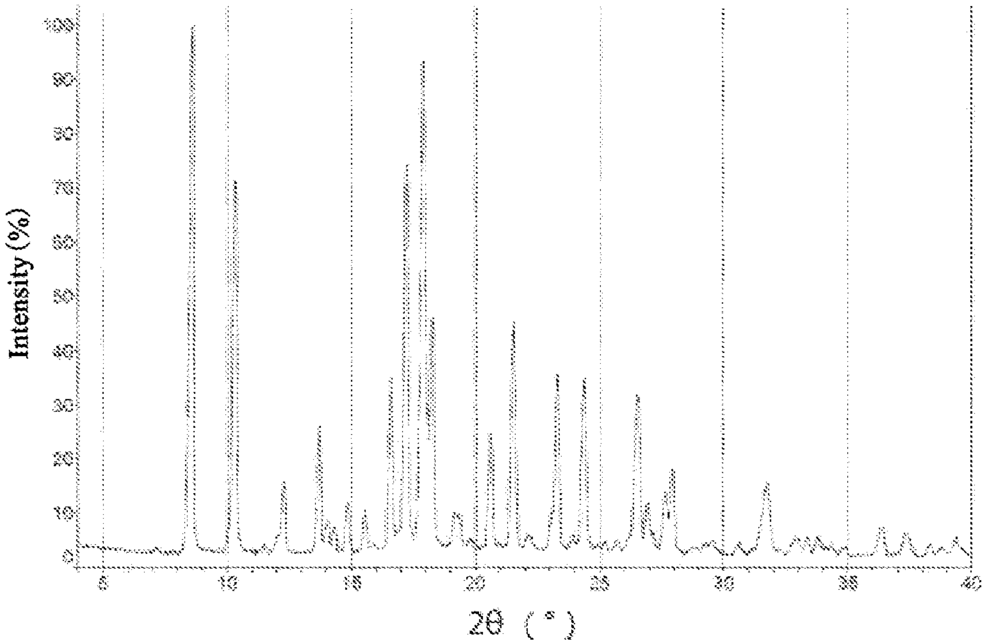
FIG. 7 is an XRPD spectrum using Cu-Kα radiation of the compound of formula (II) in crystalline form B.
Figure 8:
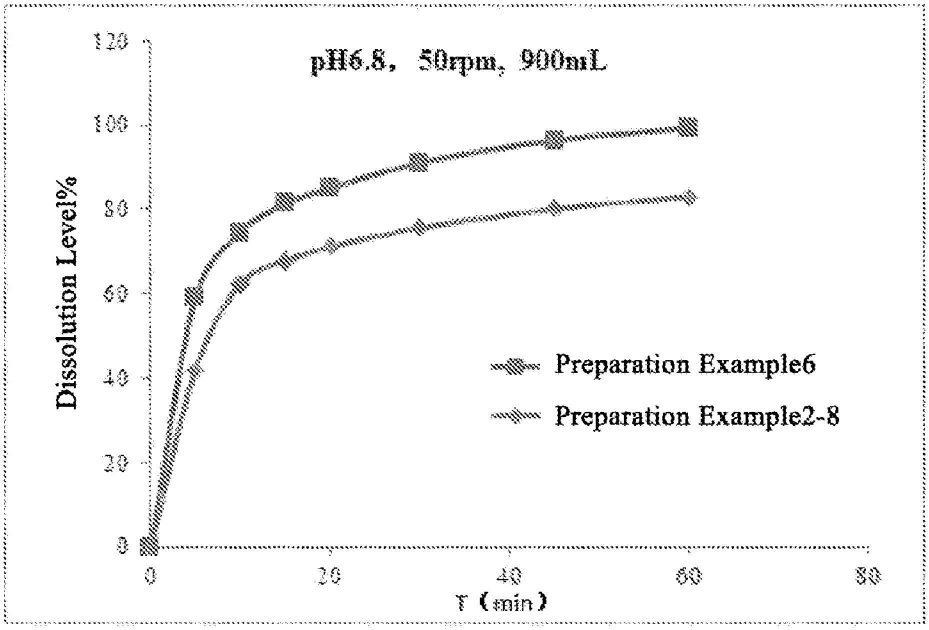
FIG. 8 is a graph showing the in vitro dissolution curves of the formulations of Preparation Examples 2-8 and Preparation Example 6, using phosphate buffer at pH 6.8 as the dissolution medium.
Figure 9:
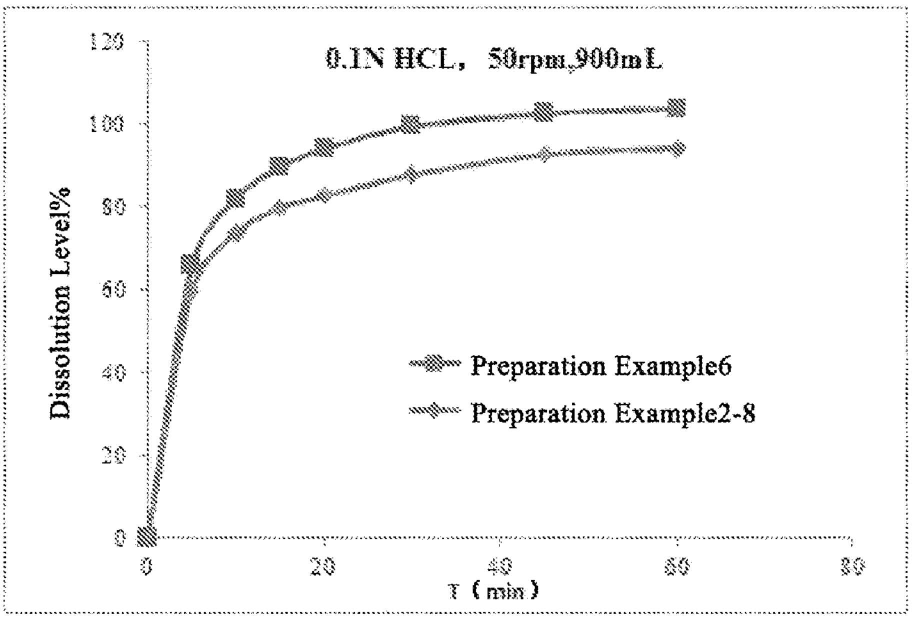
FIG. 9 is a graph showing the in vitro dissolution curves of the formulations of Preparation Examples 2-8 and Preparation Example 6, using 0.1 N HCl as the dissolution medium.
Figure 10:
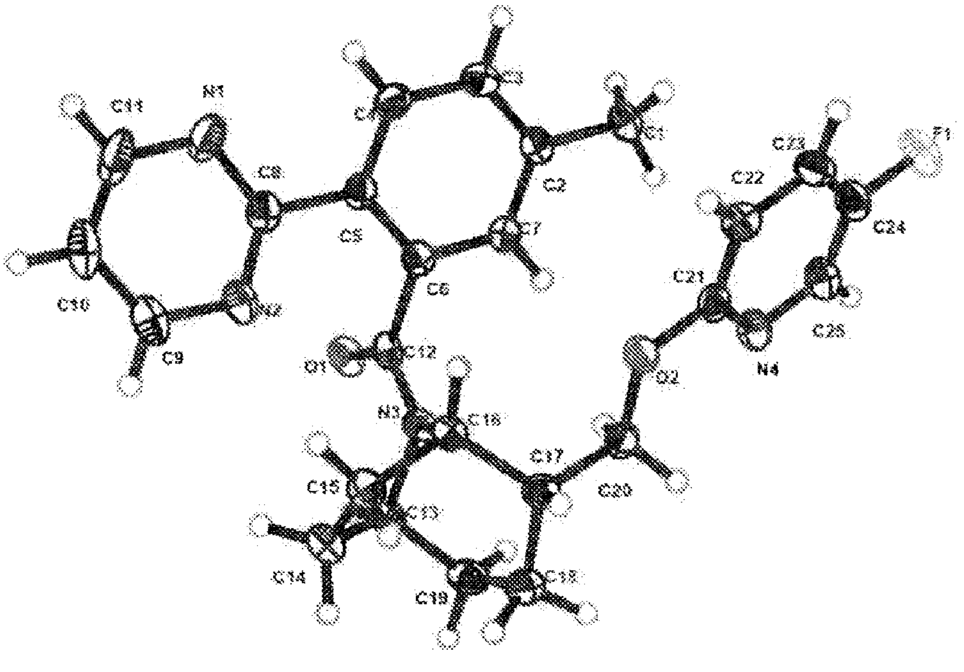
FIG. 10 is a three-dimensional ellipsoid structure of the single crystal of the compound of formula (II).

According to the second method of Chinese Pharmacopoeia 2015 4th Edition General Principles 0931, the tablet formulations prepared in the above preparation examples were subjected to an in vitro dissolution test to detect their dissolution levels in a phosphate buffer under pH 6.8, in which the dissolution device used paddle method, the dissolution medium was a pH 6.8 buffer, the water bath temperature was 37.0±0.5° C., the dissolution volume was 900 ml, the rotation speed was 50 rpm, the sampling time was 5 min, 10 min, 15 min, 20 min, 30 min, 45 min, 60 min, the sampling volume was 5 ml, and the filter membrane was polyethersulfone filter. The test results were shown in the following Tables 1-1 to 1-5 and FIGS. 1 to 5.

TABLE 1-1

In vitro dissolution results of Preparation Examples 1-1 to 1-4

| T, min | Preparation Example 1]-4 Dissolution Level, % | RSD | Preparation Example 1]-3 Dissolution Level, % | RSD | Preparation Example 1-2 Dissolution Level, % | RSD | Preparation Example 1-1 Dissolution Level, % | RSD |
|---|---|---|---|---|---|---|---|---|
| 0 | 0 | 0 | 0 | 0 | 0.0 | 0 | 0 | 0 |
| 5 | 11 | 10.1 | 35.6 | 2.6 | 29.6 | 2.1 | 38.8 | 6.5 |
| 10 | 30.3 | 48.3 | 47.5 | 4.1 | 48.0 | 1.9 | 52.5 | 2.1 |
| 15 | 27.9 | 1.2 | 54.6 | 4.5 | 58.6 | 1.0 | 61.5 | 1.8 |
| 20 | 33.3 | 3.1 | 59.3 | 0.1 | 65.9 | 0.4 | 68.2 | 0.7 |
| 30 | 41.4 | 1.3 | 66.8 | 1.0 | 75.4 | 1.2 | 75.4 | 0.6 |
| 45 | 47.1 | 0.9 | 75.7 | 0.9 | 82.0 | 0.4 | 82.4 | 0.6 |
| 60 | 51.3 | 3.9 | 79.5 | 0.7 | 86.5 | 1.0 | 86.9 | 0.8 |

TABLE 1-2

In vitro dissolution results of Preparation Examples 2-1, 2-2, 2-6 and 2-7

| T, min | Preparation Example 2-6 Dissolution Level, % | RSD | Preparation Example 2-1 Dissolution Level, % | RSD | Preparation Example 2-7 Dissolution Level, % | RSD | Preparation Example 2-2 Dissolution Level, % | RSD |
|---|---|---|---|---|---|---|---|---|
| 0 | 0 | 0 | 0 | 0 | 0.0 | 0 | 0 | 0 |
| 5 | 33.5 | 2.8 | 26.8 | 11.0 | 25.8 | 6.4 | 28.6 | 8.5 |
| 10 | 50.1 | 4.6 | 45.8 | 6.4 | 40.4 | 3.1 | 42.4 | 4.7 |
| 15 | 61.3 | 1.6 | 57.8 | 5.7 | 50.0 | 1.9 | 51.1 | 2.9 |
| 20 | 67.3 | 1.9 | 64.9 | 3.9 | 55.9 | 1.3 | 56.0 | 2.0 |
| 30 | 75.3 | 1.3 | 73.3 | 2.0 | 62.6 | 0.8 | 62.6 | 0.9 |
| 45 | 81.5 | 0.5 | 79.5 | 1.5 | 68.3 | 0.3 | 68.1 | 1.1 |
| 60 | 84.8 | 0.7 | 83.0 | 1.4 | 71.0 | 0.5 | 70.3 | 1.0 |

TABLE 1-3

In vitro dissolution results of Preparation Examples 2-1 to 2-5

| T, min | Preparation Example 2-1] Dissolution Level, % | RSD | Preparation Example 2-2 Dissolution Level, % | RSD | Preparation Example 2-3 Dissolution Level, % | RSD | Preparation Example 2-5 Dissolution level, % | RSD | Preparation Example 2-4 Dissolution Level, % | RSD |
|---|---|---|---|---|---|---|---|---|---|---|
| 0 | 0 | 0 | 0 | 0 | 0.0 | 0 | 0 | 0 | 0 | 0 |
| 5 | 33.5 | 2.8 | 25.8 | 6.4 | 29.8 | 13.3 | 13.1 | 12.2 | 17.9 | 9.3 |
| 10 | 50.1 | 4.6 | 40.4 | 3.1 | 51.8 | 4.5 | 24.3 | 6.8 | 31.9 | 3.1 |
| 15 | 61.3 | 1.6 | 50.0 | 1.9 | 63.7 | 3.3 | 32.0 | 3.3 | 40.8 | 1.5 |
| 20 | 67.3 | 1.9 | 55.9 | 1.3 | 71.5 | 2.6 | 36.7 | 2.8 | 46.7 | 0.9 |
| 30 | 75.3 | 1.3 | 62.6 | 0.8 | 80.7 | 1.7 | 44.2 | 1.2 | 55.1 | 1.2 |
| 45 | 81.5 | 0.5 | 68.3 | 0.3 | 86.8 | 1.4 | 51.4 | 1.5 | 62.5 | 0.7 |
| 60 | 84.8 | 0.7 | 71.0 | 0.5 | 90.6 | 1.5 | 56.3 | 0.8 | 67.6 | 1.8 |

TABLE 1-4

In vitro dissolution results of Preparation Examples 3, 2-1 and 2-4

| | Preparation Example 3 | | Preparation Example 2-1 | | Preparation Example 2-4 | |
|---|---|---|---|---|---|---|
| T, min | Dissolution Level, % | RSD | Dissolution Level, % | RSD | Dissolution Level, % | RSD |
| 0 | 0 | 0 | 0 | 0 | 0 | 0 |
| 5 | 38.8 | 6.5 | 33.5 | 2.8 | 17.9 | 9.3 |
| 10 | 52.5 | 2.1 | 50.1 | 4.6 | 31.9 | 3.1 |
| 15 | 61.5 | 1.8 | 61.3 | 1.6 | 40.8 | 1.5 |
| 20 | 68.2 | 0.7 | 67.3 | 1.9 | 46.7 | 0.9 |
| 30 | 75.4 | 0.6 | 75.3 | 1.3 | 55.1 | 1.2 |
| 45 | 82.4 | 0.6 | 81.5 | 0.5 | 62.5 | 0.7 |
| 60 | 86.9 | 0.8 | 84.8 | 0.7 | 67.6 | 1.8 |

TABLE 1-5

In vitro dissolution results of Preparation Examples 4-1 to 4-3

| | Preparation Example 4-1 | | Preparation Example 4-2 | | Preparation Example 4-3 | |
|---|---|---|---|---|---|---|
| T, h | Dissolution Level, % | RSD | Dissolution Level, % | RSD | Dissolution Level, % | RSD |
| 0 | 0.0 | 0 | 0.0 | 0 | 0.0 | 0 |
| 0.25 | 3.7 | 46.2 | 25.3 | 15.6 | 10.3 | 27.5 |
| 0.5 | 7.5 | 29.2 | 45.6 | 11.6 | 18.0 | 30.7 |
| 1 | 12.4 | 23.9 | 67.4 | 6.9 | 27.9 | 23.4 |
| 2 | 20.5 | 18.2 | 84.2 | 3.7 | 42.8 | 17.2 |
| 4 | 32.0 | 14.2 | 96.0 | 2.5 | 70.9 | 6.5 |
| 6 | 41.4 | 9.8 | 97.9 | 2.6 | 88.1 | 2.1 |
| 8 | 49.8 | 8.8 | 98.9 | 2.6 | 96.5 | 1.6 |
| 24 | 93.8 | 3.2 | 101.9 | 2.4 | 102.1 | 1.9 |

TABLE 1-6

In vitro dissolution results of Preparation Examples 2-8 and 6

| | pH 6.8 | | | | 0.1N HCL | | | |
|---|---|---|---|---|---|---|---|---|
| | Preparation Example 2-8 | | Preparation Example 6 | | Preparation Example 2-8 | | Preparation Example 6 | |
| ,T, min | Dissolution Level, % | RSD, % | Dissolution Level, % | RSD, % | Dissolution Level, % | RSD, % | Dissolution Level, % | RSD, % |
| 00 | 0 | 0 | 0.0 | 0 | 0 | 0 | 0.0 | 0 |
| 55 | 41.9 | 7.3 | 59.3 | 6.6 | 59.8 | 12.6 | 65.9 | 14.2 |
| 110 | 62.3 | 10.8 | 74.6 | 3.0 | 73.6 | 6.3 | 82.1 | 8.2 |
| 115 | 67.7 | 2.0 | 81.3 | 2.6 | 79.8 | 7.5 | 89.5 | 5.6 |
| 220 | 71.1 | 1.9 | 85.0 | 2.0 | 82.6 | 5.1 | 94.1 | 2.1 |
| 330 | 75.6 | 1.2 | 91.1 | 2.2 | 87.8 | 4.2 | 99.5 | 1.5 |
| 445 | 80.1 | 1.3 | 96.4 | 2.0 | 92.7 | 2.5 | 102.7 | 1.2 |
| 660 | 83.0 | 2.2 | 99.3 | 1.6 | 94.4 | 0.6 | 103.8 | 1.2 |

Test Example 2 Stability Test

After placing the prepared samples under high temperature of 60° C. and accelerated conditions (40° C./75% RH) for a certain period of time, the samples were tested for content, related substances and dissolution level according to the Second method of Chinese Pharmacopoeia 2015 $4^{th}$ Edition General Principles 0512 and 0931, to assess the stability thereof. The test results were shown in Table 2-1.

TABLE 2-1

Stability results of Preparation Examples 2-1, 2-2 and 2-4

| | | Single Impurity, % | | | | |
|---|---|---|---|---|---|---|
| Preparation Example | Conditions | Unknown Impurity RRT1.08 ≤0.30% | Other Impurities RRT1.25 ≤0.25% | Total Impurity, % ≤1.5% | Content, % | Dis-solution Level, % |
| Preparation Example 1-1 | 0 d | 0.07 | 0.14 | 0.21 | 97.7 | 84.3 |
| | 60° C., 1 M | 0.07 | 0.14 | 0.21 | 98.9 | / |
| | 40° C./75% RH, 1 M | 0.07 | 0.14 | 0.21 | 98.3 | / |
| | 60° C., 2 M | 0.04 | 0.12 | 0.16 | 98.3 | / |
| | 40° C./75% RH, 2 M | 0.04 | 0.13 | 0.17 | 98.9 | / |
| Preparation Example 2-4 | 0 d | 0.05 | 0.12 | 0.17 | 100.9 | / |
| | 60° C., 1 M | 0.06 | 0.12 | 0.18 | 98.7 | / |
| | 40° C./75% RH, 1 M | 0.06 | 0.12 | 0.18 | 97.4 | / |
| Preparation Example 2-2 | 0 d | 0.05 | 0.16 | 0.21 | 95.6 | / |
| | 60° C., 1 M | 0.05 | 0.15 | 0.20 | 96.1 | / |
| | 40° C./75% RH, 1 M | 0.05 | 0.16 | 0.21 | 97.2 | / |
| | 60° C., 2M | 0.04 | 0.13 | 0.17 | 104.1 | / |
| | 40° C./75% RH, 2 M | 0.04 | 0.13 | 0.17 | 104.3 | / |
| | 40° C./75% RH, 2 M | 0.06 | 0.13 | 0.19 | 97.7 | 87.5 |

Test Example 3 Dog Oral Bioavailability Test

A dog oral bioavailability research was performed on the prepared samples. The research was designed according to the technical guidelines for non-clinical pharmacokinetic research of the former China Food and Drug Administration (CFDA) and ICH M3(R2). The tablet has a specification of 20 mg, 1 tablet/1 dog. The samples were collected according to the designed time point. The concentrations of the active ingredients in the samples were detected by HPLC-MS/MS method, and the pharmacokinetic parameters were calculated. The specific test contents were as follows:

Animals and administration: common grade 7-14 month old Beagle dogs weight of 9.51 kg-11.14 kg were used. Oral administration was performed with single administration on each administration day with administration time 8:00-12:00. All animals were fasted overnight before each administration, and continued to fast for 2-3 hours after administration, but the total fasting time did not exceed 24 hours.

Blood collection: forelimb venous blood collection was used. Blood collection time was each administration day (i.e., Day 1, Day 5, Day 8, Day 12 and Day 15). Blood collection time points were before administration (0h), 5 min, 15 min, 30 min, 1 h, 2 h, 4 h, 6 h, 8 h and 24 h after administration. About 1 mL of blood was collected in EDTA dipotassium anticoagulant vacuum blood collection tube. After blood collection, the blood collection tube was shaken gently to mix blood and anticoagulant thoroughly. Blood was placed in crushed ice after collection, and centrifuged (4° C., 2000 g, 10 min) within 1 hour after collection. After centrifugation, about 400 μL of plasma was collected in a brown plastic tube, and immediately stored in a container of dry ice, then transferred to an ultra-low temperature refrigerator (≤−65° C.) and stored in the dark.

Sample analysis: HPLC-MS/MS method was used to detect the concentration of the active ingredients in the sample, and Microsoft Excel 2013 was used for data processing and calculation. After analyzing and measuring the concentration of samples in plasma, the concentration-time curve was plotted by WinNonlin6.3 software, and the pharmacokinetic parameters were calculated according to the non-compartmental model. The results of the pharmacokinetic parameters of the corresponding formulations are shown in the following Table 3-1, Table 3-2 and Table 3-3, respectively. The results in the same table are obtained by testing in the same batch, and the results in different tables are obtained by testing in different batches.

TABLE 3-1

Oral bioavailability of Preparation Examples 1-4, 1-3 and 1-2

| | Preparation Example | | |
|---|---|---|---|
| | Preparation Example 1-4 | Preparation Example 1-3 2 mpk | Preparation Example 1-2 |
| $AUC_{0-t}$ (hr*ng/mL) | 888 | 1537 | 2096 |
| $AUC_{0-\infty}$ (hr*ng/mL) | 1069 | 1804 | 2169 |
| $T_{max}$ (h) | 1.17 | 0.667 | 1.33 |
| $C_{max}$ (ng/mL) | 288 | 708 | 827 |
| F (%) | 53.1 | 89.7 | 108 |

TABLE 3-2

Oral bioavailability of Preparation Examples 2-1, 2-3 and 2-5

| | Preparation Example | | |
|---|---|---|---|
| | Preparation Example 2-3 | Preparation Example 2-1 | Preparation Example 2-5 |
| $T_{max}$ (h) | 1.13 ± 0.737 | 1.08 ± 0.492 | 2.25 ± 2.86 |
| $C_{max}$ (ng/mL) | 383 ± 372 | 533 ± 520 | 143 ± 103 |
| $AUC_{0-t}$ (hr*ng/mL) | 1205 ± 1032 | 1252 ± 990 | 722 ± 812 |
| $AUC_{0-\infty}$ (hr*ng/mL) | 1297 ± 1121 | 1272 ± 976 | 883 ± 1022 |

TABLE 3-3

Oral bioavailability of Preparation Examples 3, 2-1, 2-3 and 2-4

| Preparation Example | $T_{1/2}$ (h) | $T_{max}$ (h) | $C_{max}$ (ng/mL) | $AUC_{0-t}$ (ng*h/mL) |
|---|---|---|---|---|
| Preparation Example 3 | 1.38 | 0.875 | 436 | 1000 |
| Preparation Example 2-1 | 1.88 | 1.25 | 708 | 1060 |
| Preparation Example 2-4 | 6.17 | 0.875 | 393 | 901 |
| Preparation Example 2-3 | 0.79 | 1.25 | 613 | 927 |

It can be seen from the table above that different particle sizes of the active ingredient in the formulation have different effects on pharmacokinetic parameters, such as prolonged half-life or decreased exposure in Beagle dogs.

All documents mentioned in the present invention are incorporated herein by reference as if each of documents is individually incorporated by reference. In addition, it should be understood that after reading the above disclosures of the present invention, those skilled in the art can make various changes or modifications to the present invention, and these equivalent forms also fall within the scope defined by the appended claims of the present application.

The invention claimed is:

1. A solid pharmaceutical formulation, wherein the solid pharmaceutical formulation comprises an effective amount of an active ingredient, and the active ingredient is a compound represented by formula (I) or a pharmaceutically acceptable salt thereof, or a mixture of both;

(I)

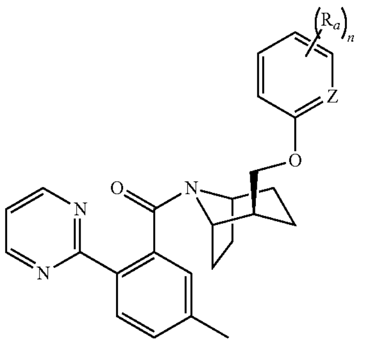

wherein $R_a$ is hydrogen, fluorine, chlorine, methyl, ethyl, propyl, isopropyl, methoxy, ethoxy, propoxy or isopropoxy; Z is N or $CR_0$; $R_0$ is hydrogen, halogen or $C_{1-3}$ alkyl; n is 0, 1 or 2;

and the particle size of the active ingredient is D90≤35 μm.

2. The solid pharmaceutical formulation according to claim 1, wherein the compound represented by formula (I) is a compound of formula (II):

(II)

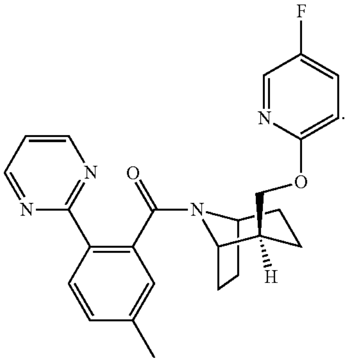

3. The solid pharmaceutical formulation according to claim 2, wherein the compound of formula (II) as the active ingredient exists in crystalline form A or crystalline form B.

4. The solid pharmaceutical formulation according to claim 1, wherein the content of the active ingredient is 1%-15% based on the total dry weight of the solid pharmaceutical formulation.

5. The solid pharmaceutical formulation according to claim 1, wherein the solid pharmaceutical formulation further comprises a binder selected from the group consisting of hypromellose, hydroxypropyl cellulose, povidone, sodium alginate, carbopol, polyvinyl alcohol and a combination thereof, wherein the content of the binder is 0.5%-10% based on the total dry weight of the solid pharmaceutical formulation; and/or wherein the solid pharmaceutical formulation further comprises a filler selected from the group consisting of microcrystalline cellulose, lactose, cellulose-lactose complex, pre-gelatinized starch, calcium hydrogen phosphate, calcium carbonate and a combination thereof, wherein the content of the filler is 60%-90% based on the total dry weight of the solid pharmaceutical formulation.

6. The solid pharmaceutical formulation according to claim 1, wherein the solid pharmaceutical formulation further comprises a disintegrant selected from the group consisting of croscarmellose sodium, hypromellose-K4M, crospovidone, sodium carboxymethyl starch and a combination thereof, wherein the content of the disintegrant is 5%-15% based on the total dry weight of the solid pharmaceutical formulation; and/or wherein the solid pharmaceutical formulation further comprises a lubricant selected from the group consisting of magnesium stearate, talcum powder, glycerol monostearate, sodium stearyl fumarate and a combination thereof, wherein the content of the lubricant is 0.1%-1% based on the total dry weight of the solid pharmaceutical formulation.

7. The solid pharmaceutical formulation according to claim 1, wherein the solid pharmaceutical formulation is a tablet, a capsule, a powder, a granule, a drop pill or a film.

8. The solid pharmaceutical formulation according to claim 1, wherein the solid pharmaceutical formulation comprises the following components based on the total dry weight of the solid pharmaceutical formulation:

a) the active ingredient: ((1S,2R,5S)-2-(((5-fluoropyridin-2-yl)oxy)methyl)-8-azabicyclo[3.2.1]octan-8-yl)(5-methyl-2-(pyrimidin-2-yl)phenyl)methanone, or a pharmaceutically acceptable salt thereof, or a mixture of both, wherein the content of the active ingredient is 1%-15%;

b) a filler selected from the group consisting of microcrystalline cellulose, lactose, cellulose-lactose complex, pre-gelatinized starch, calcium hydrogen phosphate, calcium carbonate and a combination thereof, wherein the content of the filler is 60%-90%;

c) a binder selected from the group consisting of hypromellose, hydroxypropyl cellulose, povidone, sodium alginate, carbopol, polyvinyl alcohol and a combination thereof, wherein the content of the binder is 0.5%-10%;

d) a disintegrant selected from the group consisting of croscarmellose sodium, hypromellose-K4M, crospovidone, sodium carboxymethyl starch and a combination thereof, wherein the content of the disintegrant is 5%-15%; and e) a lubricant selected from the group consisting of magnesium stearate, talcum powder, glycerol monostearate, sodium stearyl fumarate and a combination thereof, wherein the content of the lubricant is 0.1%-1%;

wherein the particle size of the active ingredient is D90≤35 μm, or D90≤30 μm, or D90≤20 μm, or D90≤10 μm, or D90=1 μm to 30 μm, or D90=1 μm to 20 μm, or D90=1 μm to 10 μm, or D90=10 μm to 20 μm.

9. The solid pharmaceutical formulation according to claim 1, wherein the solid pharmaceutical formulation comprises the following components based on the total dry weight of the solid pharmaceutical formulation:

a) the active ingredient: ((1S,2R,5S)-2-(((5-fluoropyridin-2-yl)oxy)methyl)-8-azabicyclo[3.2.1]octan-8-yl)(5-methyl-2-(pyrimidin-2-yl)phenyl)methanone, or a pharmaceutically acceptable salt thereof, or a mixture of both, wherein the content of the active ingredient is 4%-10%;

b) microcrystalline cellulose with a content of 24%-27.5%;

c) lactose with a content of 48.5%-56.5%;

d) hypromellose-E5 with a content of 1.5%-3%;

e) croscarmellose sodium or hypromellose-K4M with a content of 5%-15%; and f) magnesium stearate with a content of 0.4%-0.5%;

wherein the particle size of the active ingredient is D90≤35 μm, or D90≤30 μm, or D90≤20 μm, or D90≤10 μm, or D90=1 μm to 30 μm, or D90=1 μm to 20 μm, or D90=1 μm to 10 μm, or D90=10 μm to 20 μm.

10. The solid pharmaceutical formulation according to claim 1, wherein the solid pharmaceutical formulation comprises the following components based on the total dry weight of the solid pharmaceutical formulation:

a) the active ingredient: ((1S,2R,5S)-2-(((5-fluoropyridin-2-yl)oxy)methyl)-8-azabicyclo[3.2.1]octan-8-yl)(5-methyl-2-(pyrimidin-2-yl)phenyl)methanone, or a pharmaceutically acceptable salt thereof, or a mixture of both, wherein the content of the active ingredient is 9.5%-10%;

b) microcrystalline cellulose with a content of 24%-27.5%;

c) lactose with a content of 48.5%-56.5%;

d) hypromellose-E5 with a content of 1.5%-3%;

e) croscarmellose sodium or hypromellose-K4M with a content of 5%-15%; and f) magnesium stearate with a content of 0.48%-0.5%;

wherein the particle size of the active ingredient is D90=1 μm to 30 μm, or D90=1 μm to 20 μm, or D90=1 μm to 10 μm, or D90=10 μm to 20 μm, and the solid pharmaceutical formulation is a tablet.

11. The solid pharmaceutical formulation according to claim 1, wherein the particle size of the active ingredient is D90≤20 μm.

12. A method for treating an orexin-associated disease in a subject, comprising administering the solid pharmaceutical formulation according to claim 1 to the subject, wherein the orexin-associated disease is insomnia.

13. A method for preparing a tablet, wherein the method comprises the following steps:

(a) performing wet granulation after mixing an active ingredient particle, a filler, a binder and a first disintegrant;

(b) drying a resulting product obtained in step (a);

(c) dry-blending a resulting product obtained in step (b), a second disintegrant and a lubricant; and (d) compressing a resulting product obtained in step (c) into the tablet;

wherein the active ingredient is ((1S,2R,5S)-2-(((5-fluoropyridin-2-yl)oxy)methyl)-8-azabicyclo[3.2.1]octan-8-yl)(5-methyl-2-(pyrimidin-2-yl)phenyl)methanone, or a pharmaceutically acceptable salt thereof, or a mixture of both; and the particle size of the active ingredient particle is D90≤35 μm.

14. The method according to claim 13, wherein the content of the active ingredient is 4%-10% based on the total dry weight of the mixture obtained in step (c).

15. The method according to claim 13, wherein the content of the filler is 73%-82.5% based on the total dry weight of the mixture obtained in step (c); and/or wherein the content of the binder is 1.5%-3% based on the total dry weight of the mixture obtained in step (c).

16. The method according to claim 13, wherein the content of the first disintegrant is 2%-10% based on the total dry weight of all components in step (a), and wherein the content of the second disintegrant is 5%-10%, based on the total dry weight of all components in step (c).

17. The method according to claim 13, wherein the content of the lubricant is 0.1%-1% based on the total dry weight of all components in step (c).

18. The method according to claim 13, wherein the method further comprises:

(e) coating a resulting product obtained in step (d).

19. A unit dosage form, wherein based on a total weight of the unit dosage form, the unit dosage form comprises:

about 10 mg, about 20 mg, or about 40 mg of an active ingredient, wherein the active ingredient is a compound of formula (II);

(II)

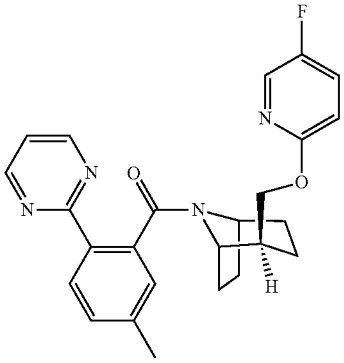

about 25 mg to about 150 mg of microcrystalline cellulose;

about 50 mg to about 300 mg of lactose;

about 1 mg to about 15 mg of hypromellose;

about 10 mg to about 50 mg of croscarmellose sodium; and about 0.5 mg to about 3 mg of magnesium stearate, wherein the particle size of the active ingredient is D90=1 μm to 20 μm; or wherein based on a total weight of the unit dosage form, the unit dosage form comprises:

8 mg to 12 mg of an active ingredient, wherein the active ingredient is a compound of formula (II);

(II)

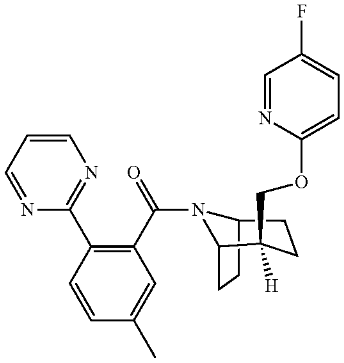

20 mg to 30 mg of microcrystalline cellulose;

46 mg to 56 mg of lactose;

2 mg to 4 mg of hypromellose;

5 mg to 15 mg of croscarmellose sodium; and 0.3 mg to 0.7 mg of magnesium stearate, wherein the particle size of the active ingredient is D90=1 μm to 20 μm; or wherein based on a total weight of the unit dosage form, the unit dosage form comprises:

18 mg to 22 mg of an active ingredient, wherein the active ingredient is a compound of formula (II);

(II)

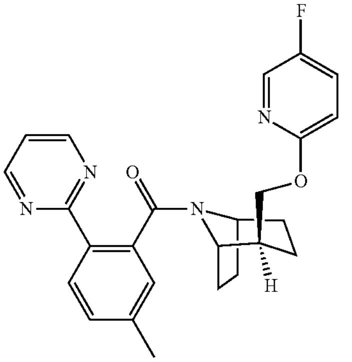

46 mg to 56 mg of microcrystalline cellulose;
97 mg to 107 mg of lactose;
5 mg to 7 mg of hypromellose;
15 mg to 25 mg of croscarmellose sodium; and
0.8 mg to 1.2 mg of magnesium stearate,
wherein the particle size of the active ingredient is D90=1 μm to 20 μm; or
wherein based on a total weight of the unit dosage form, the unit dosage form comprises:
38 mg to 42 mg of an active ingredient, wherein the active ingredient is a compound of formula (II);

(II)

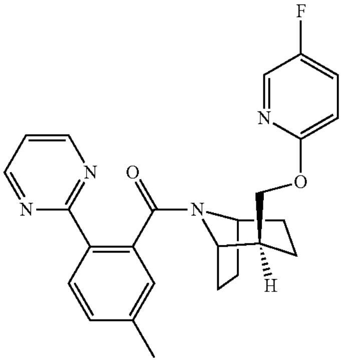

97 mg to 107 mg of microcrystalline cellulose;
199 mg to 209 mg of lactose;
11 mg to 13 mg of hypromellose;
35 mg to 45 mg of croscarmellose sodium; and
1.8 mg to 2.2 mg of magnesium stearate,
wherein the particle size of the active ingredient is D90=1 μm to 20 μm.

20. The unit dosage form according to claim 19, wherein the unit dosage form is a tablet or a capsule.

* * * * *